(12) United States Patent
Golembo et al.

(10) Patent No.: US 7,276,481 B2
(45) Date of Patent: Oct. 2, 2007

(54) METHOD AND COMPOSITION FOR TREATMENT OF SKELETAL DYSPLASIAS

(75) Inventors: Myriam Golembo, Moshav Netayim (IL); Avner Yayon, Moshav Sitria (IL)

(73) Assignee: ProChon Biotech Ltd., Ness-Ziona (IL)

( * ) Notice: Subject to any disclaimer, the term of this patent is extended or adjusted under 35 U.S.C. 154(b) by 311 days.

(21) Appl. No.: 10/664,605

(22) Filed: Sep. 15, 2003

(65) Prior Publication Data

US 2004/0138134 A1 Jul. 15, 2004

Related U.S. Application Data

(63) Continuation of application No. PCT/IL02/00229, filed on Mar. 20, 2002.

(30) Foreign Application Priority Data

Mar. 20, 2001 (IL) .................................. 00142118

(51) Int. Cl.
*A61K 38/00* (2006.01)
(52) U.S. Cl. .............................. 514/13; 514/2; 435/1.1
(58) Field of Classification Search ...................... None
See application file for complete search history.

(56) References Cited

U.S. PATENT DOCUMENTS

| | | | |
|---|---|---|---|
| 4,683,195 A | 7/1987 | Mullis et al. .................. 435/6 |
| 4,683,202 A | 7/1987 | Mullis ....................... 435/91.2 |
| 4,965,188 A | 10/1990 | Mullis et al. ................ 435/6 |
| 5,336,759 A | 8/1994 | Matsuo et al. ............... 530/326 |
| 5,338,759 A | 8/1994 | Shechter et al. ............ 514/492 |
| 5,434,133 A | 7/1995 | Tanaka et al. ................ 514/12 |
| 5,846,932 A | 12/1998 | Lowe et al. ................... 514/9 |
| 5,973,134 A | 10/1999 | Matsuo et al. ........... 536/23.53 |
| 6,020,168 A | 2/2000 | Matsuo et al. ............. 435/69.4 |
| 6,034,231 A | 3/2000 | Tanaka et al. ........... 536/23.51 |
| 6,329,375 B1 | 12/2001 | Tang et al. ................. 514/250 |
| 6,344,459 B1 | 2/2002 | Bridges et al. .......... 514/234.5 |
| 2001/0025026 A1 | 9/2001 | Heartlein et al. ............. 514/12 |

FOREIGN PATENT DOCUMENTS

EP 0 528686 A2 * 2/1993
WO WO 00/61631 10/2000

OTHER PUBLICATIONS

Druker and Lydon, J Clin Invest. 2000; 105: 3-7.*
Suzuki et al. FEBS Letters, 1991; 282: 321-325.*
Yabuta EP 0528686 A2, published Feb. 1993.*
Rivera et al. Science 2000; 287: 826-830.*
Mericq et al. J Clin Endocrinol Metab. 2000; 85: 569-73.*
Hendy et al. Kidney Int. 2006; 69: 218-223.*
Agrawal, S. et al., "Pharmacokinetics, biodistribution, and stability of oligodeoxynucleotide phosphorothioates in mice," *Proc. Natl. Acad. Sci. USA*, vol. 88, pp. 7595-7599 (1991).

Brandt, R.R. et al., "Neutral Endopeptidase Regulates C-Type Natriuretic Peptide Metabolism But Does Not Potentiate Its Bioactivity In Vivo," *Hypertension*, vol. 30, No. 2, pp. 184-190 (1997).
Chang, P.L., "Microcapsules as Bio-organs for Somatic Gene Therapy," *Annals New York Academy of Sciences*, vol. 831, pp. 460-473 (1997).
Chen, H.H. et al., "C-Type Natriuretic Peptide: The Endothelial Component of the Natriuretic Peptide Systems," *J. of Cardiovasc. Pharmacol.*, vol. 32, Suppl. 3, pp. S22-S28 (1998).
Chen, H.H. et al., "Natriuretic Peptides in the Pathophysiology of Congestive Heart Failure," *Curr. Cadiol. Rev.*, vol. 2, pp. 198-205 (2000).
Chusho, H. et al., "Dwarfism and early death in mice lacking C-type natriuretic peptide," *PNAS*, vol. 98, No. 7, pp. 4016-4021 (2001).
Fingl, E. et al., "Chapter 1—General Principles," in The Pharmacological Basis of Therapeutics 5th edition, MacMillan Publishing Co., Inc., New York, pp. 1-46 (1975).
Harvey, C.B. et al., "Molecular Mechanisms of Thyroid Hormone Effects on Bone Growth and Function," *Molecular Genetics and Metabolism*, vol. 75, pp. 17-30 (2002).
Kelly, P.A. et al., "Growth Hormone Receptor Signalling and Actions in Bone Growth," *Hormone Research*, vol. 55 (suppl. 2), pp. 14-17 (2001).
Kridel, S.J. et al., "Substrate Hydrolysis by Matrix Metalloproteinase-9," *J. Biol. Chem.*, vol. 276, No. 23, pp. 20572-20578 (2001).
Matsukawa, N. et al., "The natriuretic peptide clearance receptor locally modulates the physiological effects of the natriuretic peptide system," *Proc. Natl. Acad. Sci. USA*, vol. 96, pp. 7403-7308 (1999).
McCarthy, T.L. et al., "Local IGF-I expression and bone formation," *Growth Hormone & IGF Research*, vol. 11, pp. 213-219 (2001).
Mericq, V. et al., "Regulation of Fetal Rat Bone Growth by C-Type Natriuretic Peptide and cGMP," *Pediatric Research*, vol. 47, No. 2, pp. 189-193 (2000).
Murthy, K.S. et al., "Identification of the G Protein-activating Domain of the Natriuretic Peptide Clearance Receptor (NPR-C)," *J. Biol. Chem.*, vol. 274, No. 25, pp. 17587-17592 (1999).
Ohbayashi, H. et al., "Neutral endopeptidase 3.4.24.11 Inhibition Potentiates the Inhibitory Effects of Type-C Natriuretic Peptide on Leukotriene $D_4$-Induced Airway Changes," *Clin. Exp. Pharma. Physiol.*, vol. 25, pp. 986-991 (1998).

(Continued)

*Primary Examiner*—Elizabeth Kemmerer
*Assistant Examiner*—Christina Borgeest
(74) *Attorney, Agent, or Firm*—Winston & Strawn LLP

(57) ABSTRACT

The present invention discloses pharmaceutical compositions for the treatment of skeletal dysplasias, comprising as an active ingredient at least one natriuretic peptide. Unexpectedly, it has been shown that the natriuretic factors may be effective for bone elongation in situations of abnormal bone growth especially for achondroplasia. The effects of the natriuretic peptide may be further enhanced by prolonging its residence time or action at the target site.

30 Claims, 5 Drawing Sheets

OTHER PUBLICATIONS

Pillai, O. et al., "Polymers in drug delivery," *Curr. Opin. Chem. Biol.*, vol. 5, pp. 447-451 (2001).

Rousseau, F. et al., "Mutations in the gene encoding fibroblast growth factor receptor-3 in achondroplasia," *Nature*, vol. 371, pp. 252-254 (1994).

Schweitz, H. et al., "A New Member of the Natriuretic Peptide Family Is Present in the Venom of the Green Mamba (*Dendroaspis angusticeps*)," *J. Biol. Chem.*, vol. 267, No. 20, pp. 13928-13932 (1992).

Shiang, R. et al., "Mutations in the Transmembrane Domain of FGFR3 Cause the Most Common Genetic Form of Dwarfism, Achondroplasia," *Cell*, vol. 78, pp. 335-342 (1994).

Suda, M. et al., "Skeletal overgrowth in transgenic mice that overexpress brain natriuretic peptide," *Proc. Natl. Acad. Sci. USA*, vol. 95. pp. 2337-2342 (1998).

Vajo, Z. et al., "The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans," *Endocrine Reviews*, vol. 21, No. 1, pp. 23-39 (2000).

Van Leeuwen, J.P.T.M. et al., "24,25-Dihydroxyvitamin $D_3$ and bone metabolism," *Steroids*, vol. 66, pp. 375-380 (2001).

Yamashita, Y. et al., "Concentration of mRNA for the Natriuretic Peptide Receptor-C in Hypertrophic Chondrocytes of the Fetal Mouse Tibia," *J. Biochem.*, vol. 127, pp. 177-179 (2000).

Yasoda, A. et al., "Natriuretic Peptide Regulation of Endochondral Ossification," *J. Biol. Chem.*, vol. 273, No. 19, pp. 11695-11700 (1998).

De Feo M.L., et al., "Natriuretic hormone receptors and actions on bone endothelial cells". Endocrinology. 1993 vol. 133, No. 4, pp. 1759-1766.

Hagiwara H, et al., "cGMP produced in response to ANP and CNP regulates proliferation and differentiation of osteoblastic cells". American journal of Physiology. 1996. vol. 270, pp. C1311-1318.

Samson, W.K. Editorial: "The Power of Two-Molecular Differentiation of the Vascular and Bone Actions of the Natriuretic Peptides". Endocrinology. 2000. vol. 141, No. 10, pp. 3525-3526.

Vargas S.J., et al., "Effects of atrial natriuretic factor on cyclic nucleotides, bone resorption, collagen and deoxyribonucleic acid synthesis, and prostaglandin E2 production in fetal rat bone cultures". Endocrinology. Nov. 1989; vol. 125, No. 5, pp. 2527-2531.

\* cited by examiner

Figure 3A

CNP 1-22

CNP 5-22

Human ANP:   S L R R S S C F G G R M D R I G A Q S G L G C N S F R Y

Human BNP-32: S P K M V Q G S G C F G R K M D R I S S S G L G C K V L R R H

Human CNP 1-22: G L S K G C F G L K L D R I G S M S G L G C

Cys-Phe-Gly-Xaa-Xbb-Xcc-Asp-Arg-Ile-Gly-Xdd-Xee-Ser-Xff-Xgg-Gly-Cys

Xaa=Leu, Ile, Val; Xbb=Lys, Leu, Met; Xcc=Leu, Ile, Ala, Val;
Xdd=Ser, Ala, Gly, Thr, Asn; Xee=Met, Ala, Lys, Trp; Xff=Gly, Lys, Ala, Leu; Xgg=Leu, Met

SEQUENCE LISTING

<160> NUMBER OF SEQ ID NOS: 71

<210> SEQ ID NO 1
<211> LENGTH: 22
<212> TYPE: PRT
<213> ORGANISM: Homo sapiens
<300> PUBLICATION INFORMATION:
<308> DATABASE ACCESSION NUMBER: P23582
<309> DATABASE ENTRY DATE: 2001-10-16
<313> RELEVANT RESIDUES: (105)..(126)

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 17
<212> TYPE: PRT
<213> ORGANISM: Homo sapiens
<300> PUBLICATION INFORMATION:
<308> DATABASE ACCESSION NUMBER: P23582
<309> DATABASE ENTRY DATE: 2001-10-16
<313> RELEVANT RESIDUES: (110)..(126)

<400> SEQUENCE: 2

Cys Phe Gly Leu Lys Leu Asp Arg Ile Gly Ser Met Ser Gly Leu Gly
1               5                   10                  15

Cys

<210> SEQ ID NO 3
<211> LENGTH: 29
<212> TYPE: PRT
<213> ORGANISM: Homo sapiens
<300> PUBLICATION INFORMATION:
<308> DATABASE ACCESSION NUMBER: P01161
<309> DATABASE ENTRY DATE: 2001-10-16
<313> RELEVANT RESIDUES: (123)..(150)

<400> SEQUENCE: 3

Pro Ser Leu Arg Arg Ser Ser Cys Phe Gly Gly Arg Met Asp Arg Ile
1               5                   10                  15

Gly Ala Gln Ser Gly Leu Gly Cys Asn Ser Phe Arg Tyr
            20                  25

<210> SEQ ID NO 4
<211> LENGTH: 32
<212> TYPE: PRT
<213> ORGANISM: Homo sapiens
<300> PUBLICATION INFORMATION:
<308> DATABASE ACCESSION NUMBER: P16860
<309> DATABASE ENTRY DATE: 2001-10-16
<313> RELEVANT RESIDUES: (103)..(134)

<400> SEQUENCE: 4

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 5
<211> LENGTH: 17
<212> TYPE: PRT

```
<213> ORGANISM: Artificial Sequence
<220> FEATURE:
<223> OTHER INFORMATION: peptide variant
<220> FEATURE:
<221> NAME/KEY: MISC_FEATURE
<222> LOCATION: (4)..(4)
<223> OTHER INFORMATION: X at position 4 is defined as Xaa in the
                         specification and is either Leu (L), Ile (I) or
                         Val (V)
<220> FEATURE:
<221> NAME/KEY: MISC_FEATURE
<222> LOCATION: (5)..(5)
<223> OTHER INFORMATION: X at position 5 is defined as Xbb in the
                         description and is either Lys (K), Leu (L) or
                         Met (M)
<220> FEATURE:
<221> NAME/KEY: MISC_FEATURE
<222> LOCATION: (6)..(6)
<223> OTHER INFORMATION: X at position 6 is defined as Xcc in the
                         description and is either Leu (L), Ile (I),
                         Ala (A) or Val (V)
<220> FEATURE:
<221> NAME/KEY: MISC_FEATURE
<222> LOCATION: (11)..(11)
<223> OTHER INFORMATION: X at position 11 is defined as Xdd in the
                         description and is either Ser (S), Ala (A),
                         Gly (G), Thr (T) or Asn (N)
<220> FEATURE:
<221> NAME/KEY: MISC_FEATURE
<222> LOCATION: (12)..(12)
<223> OTHER INFORMATION: X at position 12 is defined as Xee in the
                         description and is either Met (M), Ala (A),
                         Lys (K), Trp (W).
<220> FEATURE:
<221> NAME/KEY: MISC_FEATURE
<222> LOCATION: (14)..(14)
<223> OTHER INFORMATION: X at position 14 is defined as Xff in the
                         description and is either Gly (G), Lys (K),
                         Ala (A) or Leu (L).
<220> FEATURE:
<221> NAME/KEY: MISC_FEATURE
<222> LOCATION: (15)..(15)
<223> OTHER INFORMATION: X at position 15 is defined as Xgg in the
                         specification and is either Leu (L) or Met (M).

<400> SEQUENCE: 5

Cys Phe Gly Xaa Xaa Xaa Asp Arg Ile Gly Xaa Xaa Ser Xaa Xaa Gly
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: peptide variant

<400> SEQUENCE: 6

Cys Ala Gly Leu Lys Leu Asp Arg Ile Gly Ser Met Ser Gly Leu Gly
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: peptide variant

<400> SEQUENCE: 7

Cys Phe Gly Leu Lys Leu Ala Arg Ile Gly Ser Met Ser Gly Leu Gly
1               5                   10                  15
```

Cys

<210> SEQ ID NO 8
<211> LENGTH: 17
<212> TYPE: PRT
<213> ORGANISM: Artificial Sequence
<220> FEATURE:
<223> OTHER INFORMATION: peptide variant

<400> SEQUENCE: 8

Cys Phe Gly Leu Lys Leu Asp Ala Ile Gly Ser Met Ser Gly Leu Gly
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: peptide variant

<400> SEQUENCE: 9

Cys Phe Gly Leu Lys Leu Asp Arg Ala Gly Ser Met Ser Gly Leu Gly
1               5                   10                  15

Cys

<210> SEQ ID NO 10
<211> LENGTH: 17
<212> TYPE: PRT
<213> ORGANISM: Artificial Sequence
<220> FEATURE:
<223> OTHER INFORMATION: peptide variant

<400> SEQUENCE: 10

Cys Phe Gly Leu Lys Leu Asp Arg Ile Gly Ser Ala Ser Gly Leu Gly
1               5                   10                  15

Cys

<210> SEQ ID NO 11
<211> LENGTH: 15
<212> TYPE: PRT
<213> ORGANISM: Artificial Sequence
<220> FEATURE:
<223> OTHER INFORMATION: peptide variant

<400> SEQUENCE: 11

Cys His Phe Gly Leu Lys Leu Asp Arg Ile Gly Ser Met Ser Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: peptide variant

<400> SEQUENCE: 12

Cys His Phe Gly Leu Lys Leu Asp Arg Ile Gly Ser Met Ala Cys
1               5                   10                  15

<210> SEQ ID NO 13
<211> LENGTH: 15
<212> TYPE: PRT
<213> ORGANISM: Artificial Sequence

```
<220> FEATURE:
<223> OTHER INFORMATION: peptide variant

<400> SEQUENCE: 13

Cys His Phe Gly Leu Lys Leu Asp Arg Ile Gly Ala Gln Ser Cys
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: peptide variant

<400> SEQUENCE: 14

Cys Phe Gly Leu Lys Leu Asp Arg Ile Gly Ser Met Ser Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: peptide variant

<400> SEQUENCE: 15

Cys Phe Gly Leu Lys Leu Asp Arg Ile Gly Ala Gln Ser Cys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: peptide variant

<400> SEQUENCE: 16

Cys Phe Gly Leu Lys Leu Asp Arg Ile Gly Ser Met Cys
1               5                   10

<210> SEQ ID NO 17
<211> LENGTH: 13
<212> TYPE: PRT
<213> ORGANISM: Homo sapiens

<400> SEQUENCE: 17

Cys Phe Gly Leu Lys Leu Asp Arg Ile Gly Ala Met Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide variant

<400> SEQUENCE: 18

Cys Phe Gly Leu Lys Leu Asp Arg Ile Gly Ser Gln Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: peptide variant
```

```
<400> SEQUENCE: 19

Cys Phe Gly Leu Lys Leu Asp Arg Ile Gly Ala Gln Cys
1               5                  10

<210> SEQ ID NO 20
<211> LENGTH: 13
<212> TYPE: PRT
<213> ORGANISM: Artificial Sequence
<220> FEATURE:
<223> OTHER INFORMATION: peptide variant

<400> SEQUENCE: 20

Cys His Phe Gly Leu Lys Leu Asp Arg Ile Gly Ser Cys
1               5                  10

<210> SEQ ID NO 21
<211> LENGTH: 12
<212> TYPE: PRT
<213> ORGANISM: Artificial Sequence
<220> FEATURE:
<223> OTHER INFORMATION: peptide variant

<400> SEQUENCE: 21

Cys Phe Gly Leu Lys Leu Asp Arg Ile Gly Ser Cys
1               5                  10

<210> SEQ ID NO 22
<211> LENGTH: 11
<212> TYPE: PRT
<213> ORGANISM: Artificial Sequence
<220> FEATURE:
<223> OTHER INFORMATION: peptide variant

<400> SEQUENCE: 22

Cys Phe Gly Leu Lys Leu Asp Arg Ile Gly Cys
1               5                  10

<210> SEQ ID NO 23
<211> LENGTH: 11
<212> TYPE: PRT
<213> ORGANISM: Artificial Sequence
<220> FEATURE:
<223> OTHER INFORMATION: peptide variant

<400> SEQUENCE: 23

Cys His Phe Gly Leu Lys Leu Asp Arg Ile Cys
1               5                  10

<210> SEQ ID NO 24
<211> LENGTH: 17
<212> TYPE: PRT
<213> ORGANISM: Artificial Sequence
<220> FEATURE:
<223> OTHER INFORMATION: peptide variant

<400> SEQUENCE: 24

Cys Ala Gly Leu Lys Leu Ala Arg Ile Gly Ser Met Ser Gly Leu Gly
1               5                  10                  15

Cys

<210> SEQ ID NO 25
<211> LENGTH: 17
<212> TYPE: PRT
<213> ORGANISM: Artificial Sequence
<220> FEATURE:
<223> OTHER INFORMATION: peptide variant
```

```
<400> SEQUENCE: 25

Cys Ala Gly Leu Lys Leu Asp Arg Ile Gly Ser Ala Ser Gly Leu Gly
1               5                   10                  15

Cys

<210> SEQ ID NO 26
<211> LENGTH: 17
<212> TYPE: PRT
<213> ORGANISM: Artificial Sequence
<220> FEATURE:
<223> OTHER INFORMATION: peptide variant

<400> SEQUENCE: 26

Cys Phe Gly Leu Lys Leu Ala Arg Ile Gly Ser Ala Ser Gly Leu Gly
1               5                   10                  15

Cys

<210> SEQ ID NO 27
<211> LENGTH: 17
<212> TYPE: PRT
<213> ORGANISM: Artificial Sequence
<220> FEATURE:
<223> OTHER INFORMATION: peptide variant

<400> SEQUENCE: 27

Cys Ala Gly Leu Lys Leu Ala Arg Ile Gly Ser Ala Ser Gly Leu Gly
1               5                   10                  15

Cys

<210> SEQ ID NO 28
<211> LENGTH: 17
<212> TYPE: PRT
<213> ORGANISM: Artificial Sequence
<220> FEATURE:
<223> OTHER INFORMATION: peptide variant

<400> SEQUENCE: 28

Cys Ile Gly Leu Lys Leu Asp Arg Ile Gly Ser Met Ser Gly Leu Gly
1               5                   10                  15

Cys

<210> SEQ ID NO 29
<211> LENGTH: 17
<212> TYPE: PRT
<213> ORGANISM: Artificial Sequence
<220> FEATURE:
<223> OTHER INFORMATION: peptide variant

<400> SEQUENCE: 29

Cys Leu Gly Leu Lys Leu Asp Arg Ile Gly Ser Met Ser Gly Leu Gly
1               5                   10                  15

Cys

<210> SEQ ID NO 30
<211> LENGTH: 17
<212> TYPE: PRT
<213> ORGANISM: Artificial Sequence
<220> FEATURE:
<223> OTHER INFORMATION: peptide variant

<400> SEQUENCE: 30

Cys Met Gly Leu Lys Leu Asp Arg Ile Gly Ser Met Ser Gly Leu Gly
```

```
1               5                  10                 15
Cys

<210> SEQ ID NO 31
<211> LENGTH: 17
<212> TYPE: PRT
<213> ORGANISM: Artificial Sequence
<220> FEATURE:
<223> OTHER INFORMATION: peptide variant

<400> SEQUENCE: 31

Cys Trp Gly Leu Lys Leu Asp Arg Ile Gly Ser Met Ser Gly Leu Gly
1               5                  10                 15
Cys

<210> SEQ ID NO 32
<211> LENGTH: 17
<212> TYPE: PRT
<213> ORGANISM: Artificial Sequence
<220> FEATURE:
<223> OTHER INFORMATION: peptide variant

<400> SEQUENCE: 32

Cys Val Gly Leu Lys Leu Asp Arg Ile Gly Ser Met Ser Gly Leu Gly
1               5                  10                 15
Cys

<210> SEQ ID NO 33
<211> LENGTH: 17
<212> TYPE: PRT
<213> ORGANISM: Artificial Sequence
<220> FEATURE:
<223> OTHER INFORMATION: peptide variant

<400> SEQUENCE: 33

Cys His Gly Leu Lys Leu Asp Arg Ile Gly Ser Met Ser Gly Leu Gly
1               5                  10                 15
Cys

<210> SEQ ID NO 34
<211> LENGTH: 17
<212> TYPE: PRT
<213> ORGANISM: Artificial Sequence
<220> FEATURE:
<223> OTHER INFORMATION: peptide variant

<400> SEQUENCE: 34

Cys Thr Gly Leu Lys Leu Asp Arg Ile Gly Ser Met Ser Gly Leu Gly
1               5                  10                 15
Cys

<210> SEQ ID NO 35
<211> LENGTH: 17
<212> TYPE: PRT
<213> ORGANISM: Artificial Sequence
<220> FEATURE:
<223> OTHER INFORMATION: peptide variant

<400> SEQUENCE: 35

Cys Phe Gly Leu Lys Leu Glu Arg Ile Gly Ser Met Ser Gly Leu Gly
1               5                  10                 15
Cys
```

```
<210> SEQ ID NO 36
<211> LENGTH: 17
<212> TYPE: PRT
<213> ORGANISM: Artificial Sequence
<220> FEATURE:
<223> OTHER INFORMATION: peptide variant

<400> SEQUENCE: 36

Cys Phe Gly Leu Lys Leu Gln Arg Ile Gly Ser Met Ser Gly Leu Gly
1               5                   10                  15

Cys

<210> SEQ ID NO 37
<211> LENGTH: 17
<212> TYPE: PRT
<213> ORGANISM: Artificial Sequence
<220> FEATURE:
<223> OTHER INFORMATION: peptide variant

<400> SEQUENCE: 37

Cys Phe Gly Leu Lys Leu Asn Arg Ile Gly Ser Met Ser Gly Leu Gly
1               5                   10                  15

Cys

<210> SEQ ID NO 38
<211> LENGTH: 17
<212> TYPE: PRT
<213> ORGANISM: Artificial Sequence
<220> FEATURE:
<223> OTHER INFORMATION: peptide variant

<400> SEQUENCE: 38

Cys Phe Gly Leu Lys Leu Ile Arg Ile Gly Ser Met Ser Gly Leu Gly
1               5                   10                  15

Cys

<210> SEQ ID NO 39
<211> LENGTH: 17
<212> TYPE: PRT
<213> ORGANISM: Artificial Sequence
<220> FEATURE:
<223> OTHER INFORMATION: peptide variant

<400> SEQUENCE: 39

Cys Phe Gly Leu Lys Leu Met Arg Ile Gly Ser Met Ser Gly Leu Gly
1               5                   10                  15

Cys

<210> SEQ ID NO 40
<211> LENGTH: 17
<212> TYPE: PRT
<213> ORGANISM: Artificial Sequence
<220> FEATURE:
<223> OTHER INFORMATION: peptide variant

<400> SEQUENCE: 40

Cys Phe Gly Ala Lys Leu Asp Arg Ile Gly Ser Met Ser Gly Leu Gly
1               5                   10                  15

Cys

<210> SEQ ID NO 41
<211> LENGTH: 17
<212> TYPE: PRT
```

```
<213> ORGANISM: Artificial Sequence
<220> FEATURE:
<223> OTHER INFORMATION: peptide variant

<400> SEQUENCE: 41

Cys Phe Gly Ile Lys Leu Asp Arg Ile Gly Ser Met Ser Gly Leu Gly
1               5                   10                  15
Cys

<210> SEQ ID NO 42
<211> LENGTH: 17
<212> TYPE: PRT
<213> ORGANISM: Artificial Sequence
<220> FEATURE:
<223> OTHER INFORMATION: peptide variant

<400> SEQUENCE: 42

Cys Phe Gly Val Lys Leu Asp Arg Ile Gly Ser Met Ser Gly Leu Gly
1               5                   10                  15
Cys

<210> SEQ ID NO 43
<211> LENGTH: 17
<212> TYPE: PRT
<213> ORGANISM: Artificial Sequence
<220> FEATURE:
<223> OTHER INFORMATION: peptide variant

<400> SEQUENCE: 43

Cys Phe Gly Leu Leu Leu Asp Arg Ile Gly Ser Met Ser Gly Leu Gly
1               5                   10                  15
Cys

<210> SEQ ID NO 44
<211> LENGTH: 17
<212> TYPE: PRT
<213> ORGANISM: Artificial Sequence
<220> FEATURE:
<223> OTHER INFORMATION: peptide variant

<400> SEQUENCE: 44

Cys Phe Gly Leu Met Leu Asp Arg Ile Gly Ser Met Ser Gly Leu Gly
1               5                   10                  15
Cys

<210> SEQ ID NO 45
<211> LENGTH: 17
<212> TYPE: PRT
<213> ORGANISM: Artificial Sequence
<220> FEATURE:
<223> OTHER INFORMATION: peptide variant

<400> SEQUENCE: 45

Cys Phe Gly Leu Lys Ala Asp Arg Ile Gly Ser Met Ser Gly Leu Gly
1               5                   10                  15
Cys

<210> SEQ ID NO 46
<211> LENGTH: 17
<212> TYPE: PRT
<213> ORGANISM: Artificial Sequence
<220> FEATURE:
<223> OTHER INFORMATION: peptide variant
```

```
<400> SEQUENCE: 46

Cys Phe Gly Leu Lys Ile Asp Arg Ile Gly Ser Met Ser Gly Leu Gly
1               5                   10                  15

Cys

<210> SEQ ID NO 47
<211> LENGTH: 17
<212> TYPE: PRT
<213> ORGANISM: Artificial Sequence
<220> FEATURE:
<223> OTHER INFORMATION: peptide variant

<400> SEQUENCE: 47

Cys Phe Gly Leu Lys Val Asp Arg Ile Gly Ser Met Ser Gly Leu Gly
1               5                   10                  15

Cys

<210> SEQ ID NO 48
<211> LENGTH: 17
<212> TYPE: PRT
<213> ORGANISM: Artificial Sequence
<220> FEATURE:
<223> OTHER INFORMATION: peptide variant

<400> SEQUENCE: 48

Cys Phe Gly Leu Lys Leu Asp His Ile Gly Ser Met Ser Gly Leu Gly
1               5                   10                  15

Cys

<210> SEQ ID NO 49
<211> LENGTH: 17
<212> TYPE: PRT
<213> ORGANISM: Artificial Sequence
<220> FEATURE:
<223> OTHER INFORMATION: peptide variant

<400> SEQUENCE: 49

Cys Phe Gly Leu Lys Leu Asp Lys Ile Gly Ser Met Ser Gly Leu Gly
1               5                   10                  15

Cys

<210> SEQ ID NO 50
<211> LENGTH: 17
<212> TYPE: PRT
<213> ORGANISM: Artificial Sequence
<220> FEATURE:
<223> OTHER INFORMATION: peptide variant

<400> SEQUENCE: 50

Cys Phe Gly Leu Lys Leu Asp Gln Ile Gly Ser Met Ser Gly Leu Gly
1               5                   10                  15

Cys

<210> SEQ ID NO 51
<211> LENGTH: 17
<212> TYPE: PRT
<213> ORGANISM: Artificial Sequence
<220> FEATURE:
<223> OTHER INFORMATION: peptide variant

<400> SEQUENCE: 51

Cys Phe Gly Leu Lys Leu Asp Arg Leu Gly Ser Met Ser Gly Leu Gly
1               5                   10                  15
```

Cys

<210> SEQ ID NO 52
<211> LENGTH: 17
<212> TYPE: PRT
<213> ORGANISM: Artificial Sequence
<220> FEATURE:
<223> OTHER INFORMATION: peptide variant

<400> SEQUENCE: 52

Cys Phe Gly Leu Lys Leu Asp Arg Val Gly Ser Met Ser Gly Leu Gly
1               5                   10                  15

Cys

<210> SEQ ID NO 53
<211> LENGTH: 17
<212> TYPE: PRT
<213> ORGANISM: Artificial Sequence
<220> FEATURE:
<223> OTHER INFORMATION: peptide variant

<400> SEQUENCE: 53

Cys Phe Gly Leu Lys Leu Asp Arg Thr Gly Ser Met Ser Gly Leu Gly
1               5                   10                  15

Cys

<210> SEQ ID NO 54
<211> LENGTH: 17
<212> TYPE: PRT
<213> ORGANISM: Artificial Sequence
<220> FEATURE:
<223> OTHER INFORMATION: peptide variant

<400> SEQUENCE: 54

Cys Phe Gly Leu Lys Leu Asp Arg Ile Gly Ala Met Ser Gly Leu Gly
1               5                   10                  15

Cys

<210> SEQ ID NO 55
<211> LENGTH: 17
<212> TYPE: PRT
<213> ORGANISM: Artificial Sequence
<220> FEATURE:
<223> OTHER INFORMATION: peptide variant

<400> SEQUENCE: 55

Cys Phe Gly Leu Lys Leu Asp Arg Ile Gly Gly Met Ser Gly Leu Gly
1               5                   10                  15

Cys

<210> SEQ ID NO 56
<211> LENGTH: 17
<212> TYPE: PRT
<213> ORGANISM: Artificial Sequence
<220> FEATURE:
<223> OTHER INFORMATION: peptide variant

<400> SEQUENCE: 56

Cys Phe Gly Leu Lys Leu Asp Arg Ile Gly Thr Met Ser Gly Leu Gly
1               5                   10                  15

Cys

```
<210> SEQ ID NO 57
<211> LENGTH: 17
<212> TYPE: PRT
<213> ORGANISM: Artificial Sequence
<220> FEATURE:
<223> OTHER INFORMATION: peptide variant

<400> SEQUENCE: 57

Cys Phe Gly Leu Lys Leu Asp Arg Ile Gly Asn Met Ser Gly Leu Gly
1               5                   10                  15

Cys

<210> SEQ ID NO 58
<211> LENGTH: 17
<212> TYPE: PRT
<213> ORGANISM: Artificial Sequence
<220> FEATURE:
<223> OTHER INFORMATION: peptide variant

<400> SEQUENCE: 58

Cys Phe Gly Leu Lys Leu Asp Arg Ile Gly Ser Met Ser Ala Leu Gly
1               5                   10                  15

Cys

<210> SEQ ID NO 59
<211> LENGTH: 17
<212> TYPE: PRT
<213> ORGANISM: Artificial Sequence
<220> FEATURE:
<223> OTHER INFORMATION: peptide variant

<400> SEQUENCE: 59

Cys Phe Gly Leu Lys Leu Asp Arg Ile Gly Ser Met Ser Leu Leu Gly
1               5                   10                  15

Cys

<210> SEQ ID NO 60
<211> LENGTH: 17
<212> TYPE: PRT
<213> ORGANISM: Artificial Sequence
<220> FEATURE:
<223> OTHER INFORMATION: peptide variant

<400> SEQUENCE: 60

Cys Phe Gly Leu Lys Leu Asp Arg Ile Gly Ser Met Ser Lys Leu Gly
1               5                   10                  15

Cys

<210> SEQ ID NO 61
<211> LENGTH: 17
<212> TYPE: PRT
<213> ORGANISM: Artificial Sequence
<220> FEATURE:
<223> OTHER INFORMATION: peptide variant

<400> SEQUENCE: 61

Cys Phe Gly Leu Lys Leu Asp Arg Ile Gly Ser Met Ser Gly Gln Gly
1               5                   10                  15

Cys

<210> SEQ ID NO 62
<211> LENGTH: 17
<212> TYPE: PRT
<213> ORGANISM: Artificial Sequence
```

```
<220> FEATURE:
<223> OTHER INFORMATION: peptide variant

<400> SEQUENCE: 62

Cys Phe Gly Leu Lys Leu Asp Arg Ile Gly Ser Met Ser Gly Met Gly
1               5                   10                  15
Cys

<210> SEQ ID NO 63
<211> LENGTH: 17
<212> TYPE: PRT
<213> ORGANISM: Artificial Sequence
<220> FEATURE:
<223> OTHER INFORMATION: peptide variant

<400> SEQUENCE: 63

Cys Phe Gly Leu Lys Leu Asp Arg Ile Gly Ser Met Ser Gly Ala Gly
1               5                   10                  15
Cys

<210> SEQ ID NO 64
<211> LENGTH: 17
<212> TYPE: PRT
<213> ORGANISM: Artificial Sequence
<220> FEATURE:
<223> OTHER INFORMATION: peptide variant

<400> SEQUENCE: 64

Cys Phe Gly Leu Lys Leu Asp Arg Ile Gly Ser Met Ser Gly Gly Gly
1               5                   10                  15
Cys

<210> SEQ ID NO 65
<211> LENGTH: 17
<212> TYPE: PRT
<213> ORGANISM: Artificial Sequence
<220> FEATURE:
<223> OTHER INFORMATION: peptide variant

<400> SEQUENCE: 65

Cys Phe Gly Leu Lys Leu Asp Arg Ile Gly Ser Trp Ser Gly Leu Gly
1               5                   10                  15
Cys

<210> SEQ ID NO 66
<211> LENGTH: 17
<212> TYPE: PRT
<213> ORGANISM: Artificial Sequence
<220> FEATURE:
<223> OTHER INFORMATION: peptide variant

<400> SEQUENCE: 66

Cys Phe Gly Leu Lys Leu Asp Arg Ile Gly Ser His Ser Gly Leu Gly
1               5                   10                  15
Cys

<210> SEQ ID NO 67
<211> LENGTH: 17
<212> TYPE: PRT
<213> ORGANISM: Artificial Sequence
<220> FEATURE:
<223> OTHER INFORMATION: peptide variant

<400> SEQUENCE: 67
```

```
<210> SEQ ID NO 68
<211> LENGTH: 17
<212> TYPE: PRT
<213> ORGANISM: Artificial Sequence
<220> FEATURE:
<223> OTHER INFORMATION: peptide variant

<400> SEQUENCE: 68

Cys Phe Gly Leu Lys Leu Asp Arg Ile Gly Ser Ser Ser Gly Leu Gly
1               5                   10                  15

Cys

<210> SEQ ID NO 69
<211> LENGTH: 17
<212> TYPE: PRT
<213> ORGANISM: Artificial Sequence
<220> FEATURE:
<223> OTHER INFORMATION: peptide variant

<400> SEQUENCE: 69

Cys Phe Gly Leu Lys Leu Asp Arg Ile Gly Ser Gly Ser Gly Leu Gly
1               5                   10                  15

Cys

<210> SEQ ID NO 70
<211> LENGTH: 17
<212> TYPE: PRT
<213> ORGANISM: Artificial Sequence
<220> FEATURE:
<223> OTHER INFORMATION: peptide variant

<400> SEQUENCE: 70

Cys His Gly Leu Lys Leu Asp Arg Ile Gly Ser Ala Ser Gly Leu Gly
1               5                   10                  15

Cys

<210> SEQ ID NO 71
<211> LENGTH: 17
<212> TYPE: PRT
<213> ORGANISM: Artificial Sequence
<220> FEATURE:
<223> OTHER INFORMATION: peptide variant

<400> SEQUENCE: 71

Cys Thr Gly Leu Lys Leu Asp Arg Ile Gly Ser Ala Ser Gly Leu Gly
1               5                   10                  15

Cys
```

METHOD AND COMPOSITION FOR TREATMENT OF SKELETAL DYSPLASIAS

CROSS-REFERENCE TO RELATED APPLICATIONS

This application is a continuation of the U.S. national phase of International application PCT/IL02/00229 filed Mar. 20, 2002, the content of which is expressly incorporated herein by reference thereto.

FIELD OF THE INVENTION

The present invention relates to compositions for treatment of skeletal dysplasias, such as achondroplasia, and in particular to pharmaceutical compositions for bone elongation in disorders related to abnormal bone growth comprising natriuretic peptides or natriuretic factors.

BACKGROUND OF THE INVENTION

Bone Development

Endochondral ossification is a fundamental mechanism for bone formation, whereby cartilage is replaced by bone. Endochondral ossification requires the sequential formation and degradation of cartilaginous structures that serve as molds for the developing bones. The process of endochondral ossification in the cartilaginous growth plate, which is located at both ends of vertebrae and long bones, determines longitudinal bone growth.

During fetal life and until the end of puberty, longitudinal bone growth takes place via endochondral ossification of the growth plate located at the epiphyses (ends) of long bones. The growth plate is divided into several zones of cartilage forming cells, or chondrocytes, with distinct patterns of gene expression. In the Reserve Zone, cells are small and relatively inactive. In the adjacent Proliferative Zone, chondrocytes proliferate, arrange themselves in columns and eventually undergo hypertrophy. In the lower Hypertrophic Region towards the cartilage-bone junction, cells are big and highly active but exhibit no further cell division. The matrix surrounding the hypertrophic cells calcifies and the lowermost cells undergo programmed cell death. Cell death is accompanied by the removal of the cartilaginous matrix and its replacement by bone through the concerted action of recruited bone cells, namely osteoclasts and osteoblasts.

Signaling Pathways in Bone Development

The process of endochondral ossification is the result of the concerted action of several signaling pathways. The signaling pathway triggered by activation of Fibroblast Growth Factor (FGF) receptors have been shown to be involved in several stages of limb and bone development. A number of birth defects are associated with mutations in the genes encoding FGF receptors (FGFR). For example a mutation in FGFR1 is associated with Pfeiffer syndrome. Certain other mutations in FGFR2 are associated with Crouzon, Pfeiffer, Jackson-Weiss, Apert or Beare-Stevenson syndromes. The clinical manifestation of Apert syndrome (AS) is characterized by both bony and cutaneous fusion of digits of the hands and the feet. Broad thumbs and halluces distinguish Pfeiffer syndrome, while in Crouzon syndrome limbs are normal but a high degree of proptosis is evident. The most prominent malformation syndrome associated with these mutations is craniosynostosis (the premature fusion of the skull bones sutures).

FGFR3 has an inhibitory role in bone elongation as demonstrated by the fact that mice lacking this receptor exhibit a phenotype of skeletal overgrowth. Moreover, mutations at various positions in this receptor result in skeletal dysplasias (SD). Thanatophoric dysplasia is a severe and lethal form, while hypochondroplasia is a milder form than Achondroplasia. Examination of the sequence of FGFR3 in Achondroplasia patients identified a mutation in the transmembrane domain of the receptor (reviewed in Vajo et al. (2000) Endocrine Rev 21:23-39).

Achondroplasia is the most common form of short-limbed dwarfism occurring with a frequency of 1:20,000 live births. Patients show characteristic shortening of proximal long bones (rhizomelia), relative macrocephaly, depressed nasal bridge and lumbar lordosis.

Achondroplasia is mainly caused by a Gly380Arg (G380R) mutation in the transmembrane domain of the FGFR3 and is transmitted in an autosomal dominant fashion (Shiang et al. (1994) Cell 78: 335-342 and Rousseau et al. (1994) Nature 371: 252-254). A Gly375Cys (G375C) mutation has also been reported in some Achondroplasia patients. These mutations affect the process of endochondral ossification by inhibiting proliferation and delaying maturation of chondrocytes in the growth plate cartilage of long bones, resulting in decreased elongation.

Other major regulators of bone growth include growth hormone (GH, reviewed in Kelly et al., (2001) Horm Res;55 Suppl 2:14-7); insulin-like growth factor 1 (IGF-1, reviewed in McCarthy and Centrella (2001) Growth Horm IGF Res 11:213-9), glucocorticoids (GC) thyroid hormone (TH, Harvey et al., (2002) Mol Genet Metab 75:17-30) and Vitamin D (van Leeuwen et al, (2001) Steroids 66:375-80).

Each of these molecules exerts its function by binding to specific cell-surface or nuclear receptors of skeletal cells.

Natriuretic Peptides

Natriuretic peptides are known for their role in cardiovascular homeostasis, diuresis, natriuresis and vasodilation. Four isoforms constitute this family: atrial natriuretic peptide (ANP), brain natriuretic peptide (BNP), C-type natriuretic peptide (CNP) and dendroaspis natriuretic peptide (DNP). While ANP and BNP are circulating peptides produced by the atria and the ventricle respectively, CNP is hardly found in circulation and is mainly produced in the brain, in vascular endothelial cells and other tissues where it is supposed to work in an autocrine/paracrine manner (Chen and Burnett (1998) J. Cardiovasc. Pharm. 32 Suppl 3:S22-8). DNP is present in human plasma and atrial myocardium (Chen et al (2000) Curr Cardiol 2:198-205) and its sequence disclosed (Schweltz et al (1992) JBC 267:13928-32). CNP from different species have been disclosed in U.S. Pat. No. 5,336,759 (frog); U.S. Pat. No. 5,338,759 (chicken); U.S. Pat. No. 5,973,134 (rat); U.S. Pat. No. 6,020,168 (pig) and U.S. Pat. No. 6,034,231 (human).

Natriuretic peptides effect their biological role through two receptors: NPR-A and NPR-B. These receptors have cytoplasmic guanylyl cyclase domains, which are activated upon ligand binding and lead to accumulation of intracellular cGMP. Some of the effects of cGMP are mediated through two known protein kinases: cGMP-dependent protein kinase I and II. The peptides bind the receptors with different affinities: $ANP \geq BNP >> CNP$ for NPR-A and $CNP > ANP \geq BNP$ for NPR-B. The tissue distribution of each receptor is different. While NPR-A is expressed in vasculature, kidney and adrenal glands, NPR-B is mainly expressed in the brain.

NPR-C, a third receptor devoid of the kinase and cytoplasmic GC domains is generally considered to be a clearance receptor for removing natriuretic peptides from the circulation, though some other biological functions have been attributed to it (Murthy and Makhlouf (1999) JBC 274:17587-92). This is a widely distributed receptor expressed in almost all the tissues that express a guanylyl cyclase receptor. U.S. Pat. No. 5,846,932 discloses potent ANP variants having decreased affinity for the human clearance or C-receptor. These ANP variants exhibit natriuretic, diuretic and vasorelaxant activity but have increased metabolic stability, making them suitable for treating congestive heart failure, acute kidney failure and renal hypertension. Furthermore, WO00/61631 discloses novel pentapeptide antagonists of the NPR-C.

Natriuretic peptides have a short half life in vivo. In addition to the clearance receptor, they are further cleared from the circulation by degradation. The peptides are cleaved at specific sites, by the neutral endopeptidase 24.11 (NEP) which is found in endothelial cells covering the vascular walls. Human BNP is more resistant to this degradation while ANP and CNP are readily degraded by this enzyme. Inhibition of NEP by inhibitors, including the compounds thiorphan or candoxatril (Ohbayashi et al. (1997) Clin. Exp. Pharma. Physiol. 25: 986-91; Brandt et al. (1997) Hyperten. 30: 184-90), increases the concentration of endogenous or administered peptides in the circulation.

CNP, like ANP, BNP and DNP, was shown to exhibit natriuretic and hypotensive actions. Novel CNP-related peptides capable of eliciting a strong cGMP response and suppressing the growth of vascular smooth muscle cells have been disclosed in U.S. Pat. No. 5,434,133. Also disclosed are the amino acids responsible for the cGMP producing activities and novel CNP variants capable of inhibiting abnormal growth of smooth muscle cells, for the treatment of, inter alia, restenosis and arteriosclerosis.

Transgenic mice, over-expressing BNP show a skeletal phenotype characterized by overgrowth of the axial and appendicular skeleton (Suda et al. (1998) PNAS 95: 2337-42). Moreover, mice that are null mutants for the clearance receptor, NPR-C, exhibit similar skeletal overgrowth, consistent with a role for the local modulation of natriuretic peptides levels by NPR-C (Matsukawa et al. (1999) PNAS 96: 7403-08). CNP and its specific receptor, NPR-B, have been shown to be expressed in the proliferating zone of the growth plate in fetal mouse tibia while NPR-C has been shown to be expressed in the region of hypertrophic chondrocytes and in osteoblasts (Yamashita et al. (2000) J Biochem 127: 177-9). After the date of the present invention, Chuso et al (Chusho et al. (2001) PNAS 98:4016-21) have disclosed CNP knockout mice which exhibit skeletal phenotypes histologically similar to those seen in A chondroplasia mice. They also reveal the rescue of the CNP knock out skeletal defects by tissue-specific ectopic CNP expression in the growth plate. Moreover, ex vivo experiments (fetal bone organ culture) from wild type animals have shown that CNP, more than BNP and ANP, can induce bone elongation (Yasoda et al. (1998) JBC 273: 11695-700, Mericq et al. (2000) Ped Res 47: 189-93).

While much is known about the components of signaling pathways that contribute to the process of endochondral ossification, little is known about the complex interactions between them that coordinate longitudinal bone growth.

SUMMARY OF THE INVENTION

The present invention sets out to provide a method for the treatment of skeletal dysplasias. The present invention also provides pharmaceutical compositions useful in the treatment of skeletal dysplasias. Yet novel compounds and compositions useful in the methods of the invention are also provided.

The method and composition of the invention affect bone elongation, inter alia, by increasing the size of the growth plate of the bone, specifically of limb bones, in skeletal dysplasias such as achondroplasia.

The present invention provides a pharmaceutical composition comprising natriuretic peptides (NP) or functional variants useful in effecting bone elongation and treating skeletal dysplasias.

The present invention also provides NP variants with increased stability.

The present invention further provides a method to enhance NP stabilization in circulation.

Still, the present invention provides a method of delivering NP or its variants to a target site.

The invention provides the methods of effecting bone elongation and treating skeletal dysplasias which comprise using natriuretic peptides (NP), their conjugates, variants and derivatives in.

The method of the invention for treating skeletal dysplasias includes the step of administering to a patient an effective amount of an NP. In one currently preferred embodiment of the present invention the natriuretic peptide is CNP. In another currently preferred embodiment the natriuretic peptide is a CNP variant. The method may further include a step of administering to the patient an inhibitor of neutral endopeptidase 24.11 (NEP). Suitable compounds for inhibiting NEP are known in the art, including but not limited to thiorphan or candoxatril. Administration of such an inhibitor of neutral endopeptidase may be performed either separately or simultaneously with the administration of NP. It may also include administering a clearance receptor (NPR-C) inhibitor either alone or in conjunction with administration of NP.

Hyperactivation of the FGFR pathways has been implicated in several bone skeletal dysplasias. In particular, over stimulation of FGFR3 results in bone growth inhibition. The method of the invention for treating skeletal dysplasias includes administering to a patient a pharmaceutical composition comprising an NP and a receptor kinase inhibitor, in particular a tyrosine kinase inhibitor including, but not limited to, those disclosed in U.S. Pat. Nos. 6,329,375 or 6,344,459.

In another currently preferred embodiment NP is targeted to a desired tissue, specifically the growth plate of the bones. This may be achieved by methods known to one skilled in the art and include, in a nonlimiting manner, a chimeric protein comprising an NP fused to a carrier domain to form a fusion protein. The NP includes all forms of the NPs, CNP and derivatives or variants. A carrier domain includes, for example, a hormone or a ligand for a receptor expressed in the target tissue. The carrier protein may be an active agonist or an inactive targeting moiety or a variant or mutant thereof. According to one currently preferred embodiment CNP or a functional variant is fused to growth hormone. An alternative embodiment comprises conjugating at least one NP to a carrier protein to form an NP-carrier protein conjugate.

Alternatively, NP maybe conjugated to an agent to prolong its half life in circulation or to a peptide that facilitates translocation across a cell membrane.

Administration of NP to a patient can be achieved by any suitable route of administration, including but not limited to injecting NP to the patient, inhalation, or implantation of a depot into the patient. The depot is preferably implanted at the site of the lesion, the lesion being an abnormal bone or a dysplasic bone. The NP may further be administered by an osmotic pump, such as an Alzet pump. The osmotic pump can be implanted subcutaneously, or at any other appropriate site. Preferred sites may be close to the target site of action namely in proximity to the long bones of the limbs, and in particular near the epiphyses.

A further method of administration may be implantation of NP secreting cells. According to one currently preferred embodiment of the invention the NP is CNP. The NP may be natural or a variant or analog. The methods of implanting or transplanting living cells to provide therapeutically useful substances (cell therapy) is known in the art. In one form of cell therapy, the cells that are implanted have been genetically modified in vitro with exogenous genetic material so as to enable the cells to produce a desired biological substance that is useful as a therapeutic agent. Methods of genetically engineering cells are known to those skilled in the art. Methods for implantation or transplantation of NP secreting cells include encapsulation of the cells in any immunologically inert matrix including gelatin or polymers. According to one currently preferred embodiment the matrix is an alginate-polylysine-alginate (APA) complex encapsulating the cells. These methods of administration and other known methods may be utilized alone or in combination for treating skeletal dysplasia.

The present invention further provides a composition for treatment of skeletal dysplasias, such as achondroplasia. The composition includes an NP or NP variant and any pharmaceutically acceptable diluent or carrier thereof. According to one currently preferred embodiment of the invention, the natriuretic peptide is a BNP. According to one currently more preferred embodiment of the invention the natriuretic peptide is a CNP. According to one currently most preferred embodiment of the invention the natriuretic peptide is a CNP variant. The composition may further include any substance, molecule or vehicle capable of increasing the NP stability in vivo. For example the composition may include an inhibitor of neutral endopeptidase 24.11 (NEP), including but not limited to thiorphan or candoxatril. In another embodiment the composition may include an inhibitor of the natriuretic peptide receptor-C (NPR-C).

The composition may be in any form suitable for being administered to a patient, including but not limited to in dry, liquid or suspension form or injectable, implantable or transplantable form.

Also provided is a composition for treatment of skeletal dysplasias that includes NP secreting cells encapsulated within an immunologically inert matrix. One currently preferred embodiment includes NP secreting cells encapsulated in an alginate-polylysine-alginate (APA) complex and a suitable carrier thereof.

According to one currently preferred embodiment of the present invention natriuretic peptides and variants thereof are provided for the treatment of skeletal dysplasias. In another currently preferred embodiment of the present invention the NP is CNP and novel CNP variants. The peptide variants have been modified by removing the five N-terminal amino acids of CNP, considered to be a part of the ectocyclic domain and have further been modified by amino acid substitutions. According to one currently more preferred embodiment of the present invention the variant CNP comprises 17 amino acids, from Cysteine5 to the Cysteine22 as depicted in FIG. 3B, and is identified herein as SEQ ID NO:2. According to one currently most preferred embodiment of the present invention the variant CNP comprises 17 amino acids and an amino acid substitution at a cleavage site, and is depicted as SEQ ID NO:5

Cys-Phe-Gly-Xaa-Xbb-Xcc-Asp-Arg-Ile-Gly-Xdd-
Xee-Ser-Xff-Xgg-Gly-Cys wherein
Xaa=Leu, Ile, Val; Xbb=Lys, Leu, Met; Xcc=Leu, Ile, Ala, Val; Xdd=Ser, Ala, Gly, Thr, Asn; Xee=Met, Ala, Lys, Trp; Xff=Gly, Lys, Ala, Leu; Xgg=Leu, Met.

Accordingly, one currently preferred embodiment of the present invention is the variant having SEQ ID NO:10 wherein Met17 has been substituted with various amino acids and exhibits high cGMP activity. A currently preferred embodiment of the present invention provides a CNP variant comprising a Met17 substitution.

BRIEF DESCRIPTION OF THE DRAWINGS

The present invention will be understood and appreciated more fully from the following detailed description taken in conjunction with the drawings in which:

FIG. 1A shows the growth rate during the first three days of culture. FIG. 1B shows the growth rate during days 3-15.

FIG. 2A depicts the interpolation of the growth rate curves of FIG. 1. FIG. 2B shows the growth rates of CNP or vehicle treated femora derived from wild type, Ach heterozygotes and Ach homozygotes.

FIGS. 3A-C show the amino acid sequences of the NPs and the NEP cleavage sites for CNP. The endocyclic sequences are underlined. The amino acids are represented by either the one-letter code or three-letter codes according to IUPAC conventions. FIG. 3A shows the native human CNP 1-22 peptide with the NEP cleavage sites marked with an arrow. FIG. 3B shows the amino acid sequence of CNP-5-22. FIG. 3C shows the alignment of human ANP, BNP and CNP peptides and the amino acid sequence of the variants of the present invention.

DETAILED DESCRIPTION OF THE INVENTION

Figure 1A:
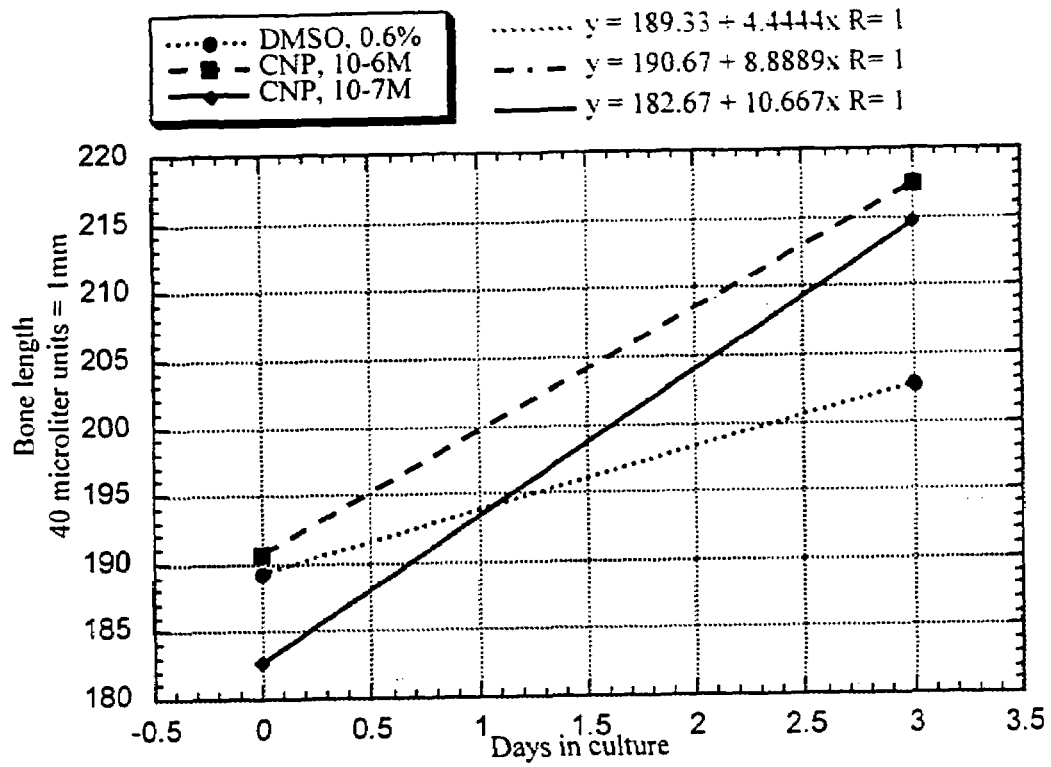
FIGS. 1A and 1B show the growth rate curves for CNP treated Ach heterozygote femora in the ex vivo experiment.

Achondroplasia is characterized, inter alia, by shortening of proximal long bones. In humans the bone growth plate is active until puberty and bone growth is thus achieved until puberty. Thus, treatment aimed at bone elongation, for example, by increasing the size of limb bone growth plate, would be advantageous during this period.

Treatment of skeletal dysplasias such as achondroplasia, includes treating a shortened bone with NP. The bone may be treated by administering to a patient an effective amount of NP. The amount of the active ingredient administered will be determined by the attending physician and is generally proportional to the patient's weight.

According to the present invention it is now disclosed that NP can induce bone elongation in situations of abnormal bone growth such as those typical of skeletal dysplasias.

The role and use of NPs in bone elongation in situations of abnormal bone growth and in the treatment of skeletal dysplasias, such as achondroplasia, is demonstrated in the following examples and experiments.

For convenience certain terms employed in the specification, examples and claims are described here.

The term "natriuretic peptides" or "NP" as referred to herein and in the claims relates to any of the three isoforms, atrial natriuretic peptide (ANP), brain natriuretic peptide (BNP), C-type natriuretic peptide (CNP) and dendroaspis natriuretic peptide (DNP) and to any functional variants thereof. The NP may be of any species but is preferably human.

The term "FGFR" as used herein denotes a receptor specific for FGF which is necessary for transducing the signal exerted by FGF to the cell interior, typically comprising an extracellular ligand-binding domain, a single transmembrane helix, and a cytoplasmic domain that contains a tyrosine kinase activity.

A "ligand" as used herein is a molecule capable of binding a receptor or a receptor analog. The ligands of the hGh-R (human growth hormone receptor) and FGFRs are the hGH and FGF molecules or variants thereof. The molecule may be chemically synthesized, synthesized by recombinant techniques or may occur in nature.

The terms "variant", "derivative" or "mutant" as used herein interchangeably refer to a polypeptide sequence that possesses some modified structural property of the native sequence. For example, the variant may be truncated at either the amino or carboxy termini (N- or C-termini) or both termini or may have amino acids deleted or substituted. It is contemplated in this invention that a variant may have altered binding to a receptor than the native protein. It may have enhanced or reduced binding which may enhance or depress a biological response. A biological response may be, for example, the stimulation of cell division, differentiation, homeostasis or growth. A biological response may encompass other functional properties of the native protein and would be well known to those practicing the art. Accordingly, the variant may have altered specificity for one or more receptors. The variant may be generated through recombinant DNA technologies, well known to those skilled in the art.

As used herein, the term "polymerase chain reaction" ("PCR") refers to the methods disclosed in U.S. Pat. Nos. 4,683,195, 4,683,202, and 4,965,188, hereby incorporated by reference.

Pharmacology

The present invention also contemplates pharmaceutical formulations, both for veterinary and for human medical use, which comprise as the active agent one or more peptide(s) of the invention, as well as the use of a peptide of the invention in the manufacture of a medicament for the treatment or prophylaxis of the skeletal conditions variously described herein.

In such pharmaceutical and medicament formulations, the active agent preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose. The pharmaceutical composition of the present invention can be administered either as free forms of the peptides of the present invention or as pharmacologically acceptable acid addition salts thereof.

The dose of the pharmaceutical composition of the present invention may vary with the kind of disease, the age of patient, body weight, the severity of disease, the route of administration, etc.; typically, it can be administered in a daily dose of 0.5-500 microgr/kg.

Apart from other considerations, the fact that the novel active ingredients of the invention are peptides, peptide variants or fusion proteins dictates that the formulation be suitable for delivery of these types of compounds. Clearly, peptides are less suitable for oral administration due to susceptibility to digestion by gastric acids or intestinal enzymes. The peptide analogs of the present invention have been designed to circumvent these problems. The preferred routes of administration of peptides are intra-articular, intravenous, intramuscular, subcutaneous, intradermal, or intrathecal. A more preferred route is by direct injection at or near the site of disorder or disease. Alternatively, they may be administered per orally as microcapsules in which the peptides of the present invention are incorporated as the active ingredient in liposome, polyamide, etc. and which are rendered resistant to degradation in the digestive tract. Another method of administration that can be adopted is to have the drug absorbed through the mucous membrane such as in the rectum, within the nose or eye or beneath the tongue, so that the drug is administered as a suppository, intranasal spray, eye drop or sublingual tablet.

In one currently preferred embodiment of the present invention, cells genetically engineered to express high levels of an NP or an NP variant are provided. Said cells may be implanted at a suitable location, more preferably at or near the intended site of activity, most preferably at or near an affected limb bone. In a currently more preferred embodiment, the cells are encapsulated. The encapsulated cells may be implanted at a suitable location, more preferably at or near the intended site of activity within the body. Implantation is preferably subcutaneous, at a site in close proximity to the growth plate of limb bones.

As used herein a "pharmaceutical composition" refers to a preparation of one or more of the peptides or peptide analogs selected from the sequences described herein, or physiologically acceptable salts or prodrugs or fusion proteins thereof, with other chemical components such as physiologically suitable carriers and excipients. The purpose of a pharmaceutical composition is to facilitate administration of a compound to an organism.

The term "prodrug" refers to an agent, which is converted into an active drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Pharmaceutical compositions may also include one or more additional active ingredients.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al, (2001) Curr Opin Chem Biol 5:447-51). Optionally, the suspension may also contain suitable stabilizers or agents which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The formulations of present invention may be administered topically as a gel, ointment, cream, emulsion or sustained release formulation including a transdermal patch. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Administration may be preferred locally by means of a direct injection at or near the site of target or by means of a patch or subcutaneous implant, staples or slow release formulation implanted at or near the target.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (Fingl, et al. (1975) in "The Pharmacological Basis of Therapeutics", Ch. 1 p.1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

Utilities

The present invention also relates to methods of treatment of skeletal disorders described above, by administering to a patient in need thereof a therapeutically effective amount of the compositions of the present invention. The term administration as used herein encompasses oral, parenteral, intravenous, intramuscular, subcutaneous, transdermal, intrathecal, rectal, intralesional and intranasal administration.

The present invention further relates to method for the use of the NP or peptide variants, conjugates or fusions of the present invention to prepare medicaments useful in the treatment of various skeletal disorders such as Achondroplasia and thanatophoric dysplasia.

EXAMPLES

Example 1

Ex Vivo Bone Culture

Femora derived from achondroplasia model mice (Ach369 knock-in mice carry the Gly to Cys mutation at position 369, analogous to position 375 in humans or Ach374 knock-in mice that carry the Gly to Arg mutation at position 374, analogous to position 380 in humans) were dissected from P0 wild type, heterozygote and homozygote littermates and cultured in the presence of natriuretic peptides for 15 days.

Protocol for Bone Culture: Femoral bone cultures were performed by excising the hind limbs of mice. The limbs were carefully cleaned from the surrounding tissue (skin and muscles) and the femora exposed. The femora were removed and further cleared from tissue remains and ligaments. The femora were measured for their initial length, using a binocular with an eyepiece micrometer ruler. The bones were grown in 1 ml of medium (α-MEM supplemented with penicillin (100 units/ml), streptomycin (0.1 mg/ml), nystatin (12.5 units/ml), BSA (0.2%), β-glycerophosphate (1 mM) and freshly prepared ascorbic acid (50 μg/ml)) with varying concentrations of NPs or CNP variants in a 24 well tissue culture dish. The bones were cultured for 15 days while measurements of bone length and medium replacement were performed every three days. At the end of the experiment, the growth rate of the bones was determined. The growth rate of bones is calculated from the slope of a linear regression fit on the length measurements obtained from day 3 to 15. Units given can be converted to length, 40 units=1 mm.

Results: Ex vivo experiments with fetal bone organ culture from wild type (normal) animals have shown that CNP, more than BNP and much more than ANP, can induce bone elongation. According to the present invention it is now shown that natriuretic peptides can induce longitudinal growth of Achondroplasia-derived bones. CNP increased the total longitudinal growth of femora derived from Ach374/+, Ach369/Ach369, Ach369/+ and wild type (+/+ or wt) mice compared to vehicle treated animals.

Figure 1B:
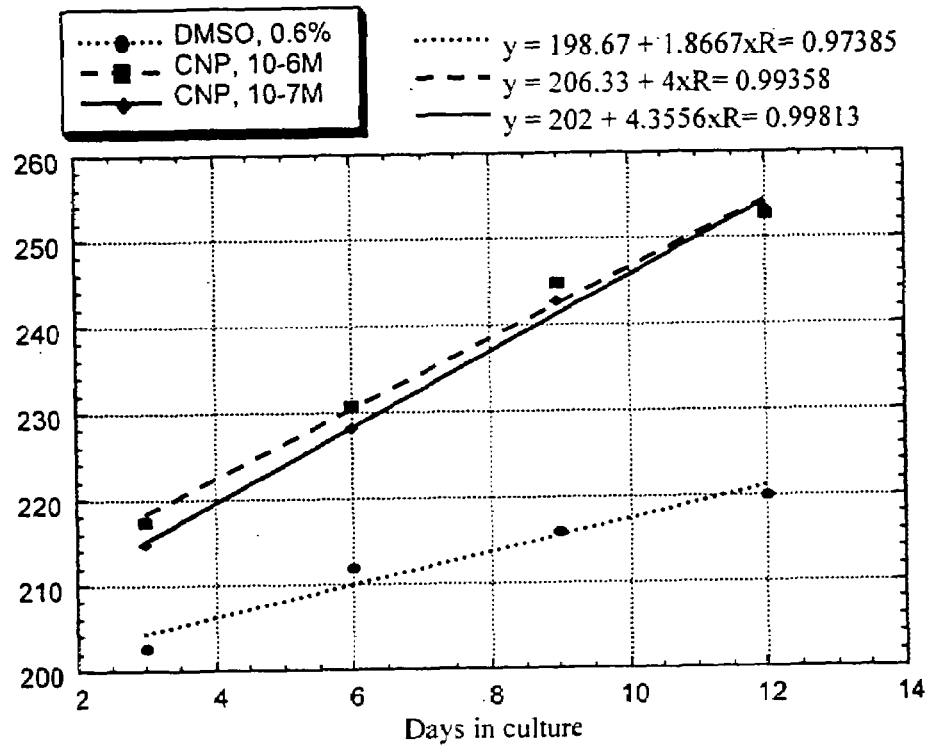
Figure 2A:
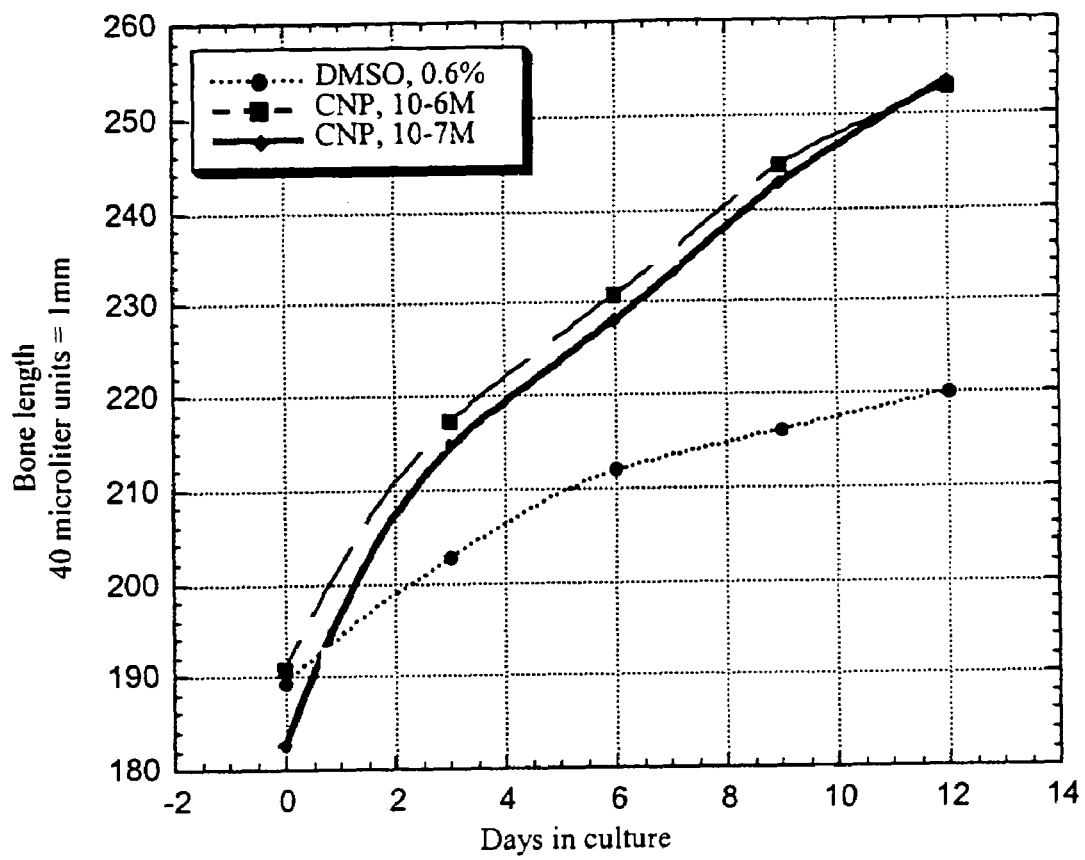
FIGS. 2A and 2B show growth rates of femora ex vivo.

FIGS. 1A and 1B depict the growth rate curves for the CNP treated Ach heterozygote femora in the experiment. FIG. 2A shows the interpolation of the rates in FIGS. 1A-B. The growth rate curves shows two stages of growth: an initial stage (days 0-3) in which growth is quick and is most affected by the presence of natriuretic peptides and a second slower linear rate. The maximal growth rate is observed in the initial days of culture. This may be due to the limitations of the culturing conditions, particularly to the depletion of nutrients.

Figure 2B:
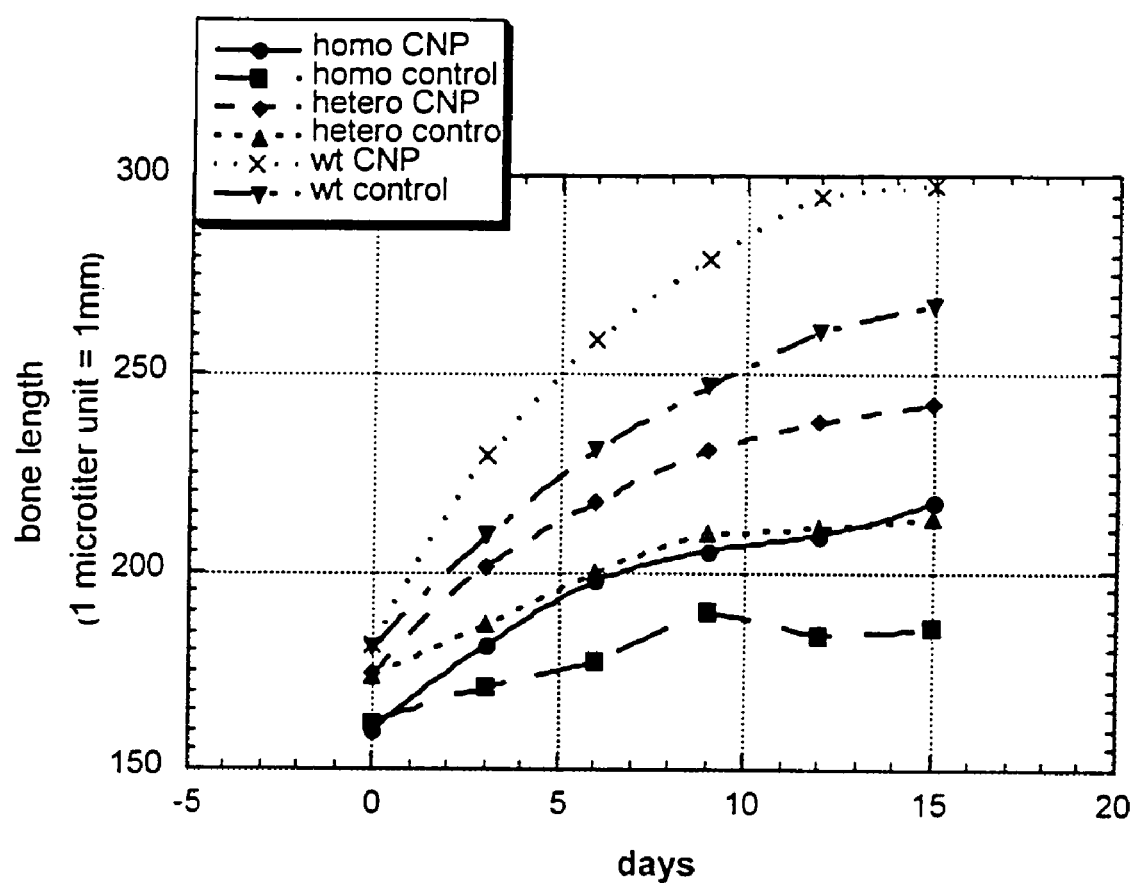

FIG. 2B shows the growth rate over 15 days in the homozygote mutant and heterozygote mutant femoras compared to wt femoras. In all cases, the CNP treated femoras increased in size at a rate higher than that of the untreated limbs. The final length if the bone was greater in the CNP treated groups, as well. These results suggest that Achondroplasia derived rudiments have a high capacity to respond to CNP and are able to reach a growth rate similar to that of the wt.

Interestingly, at this stage, femora derived from homozygote Ach animals respond better to CNP than femora derived from heterozygote animals while bones derived from wt animals are very slightly influenced by CNP. This is summarized in Table 1.

TABLE 1

Growth rate of femora in CNP treated mice

| CNP | Growth rate (days 0-3) | | Growth rate (days 3-15) | |
|---|---|---|---|---|
| | untreated | treated | untreated | treated |
| +/+ wild type (wt) | 9 | 10 | 4.9 | 5.7 |
| Ach/+ heterozygote | 4.4 | 9.1 | 2.1 | 3.4 |
| Ach/Ach homozygote | 2.9 | 7.1 | 1.2 | 2.8 |

Example 2

Natriuretic Peptides Lead to an Increase in the Size of Growth Plate:

Morphological and Immunohistological Analysis

Most of the elongation induced by natriuretic peptides observed in bone culture results from epiphyseal growth and not from elongation of the mineralized diaphysis. Morphological analysis of the cellular composition of the growth plate in treated samples revealed that there is an increase in the size of the proliferative region and in the size of the hypertrophic zone. In addition, there is an area of acellular matrix similar to that observed in the growth plate of FGFR3 knockout mice. Therefore, there seems to be an increase in proliferation which leads to a larger growth plate.

Mouse-specific BNP was synthesized and labeled with biotin. Biotinylated BNP was tested in bone culture on bones derived from Achondroplasia mice and shown to induce bone elongation. Nevertheless, a higher concentration of BNP was needed. Histological analysis of the distribution of biotinylated BNP in the growth plate shows that it is apparent both in proliferative and in hypertrophic cells. Recent studies have shown the distribution of the NP receptors in the growth plate: NPR-B is expressed in proliferative cells while NPR-C is expressed in hypertrophic cells (Yamashita et al. (2000) J. Biochem 127: 177-179). Therefore, BNP could exert its effect on bone growth either by stimulating the activity of NPR-B or by blocking the clearance of the endogenous peptide, CNP, through NPR-C.

Several signaling pathways contribute to the process of endochondral ossification. The epistatic relationship between the natriuretic peptide and the FGF signaling pathways is not known. The pathways could act in parallel or one could act to induce the other. For example, if the FGF pathway were epistatic (downstream), to the NP pathway, an increase in the activity of NP would not result in a rescue of the FGFR defects. Furthermore, if the pathways acted in parallel it would not be obvious that an increase in NP signaling would be able to overcome the effect of the FGFR mutations.

Experiment 3

In Vivo Administration

1. IP Administration of Drugs to Achondroplasia Pups

The fastest growth period for mice is during the first month of life therefore, it is expected that the earlier the experiments are initiated, the greater the influence on growth. The disadvantage of treating such young animals is that there is a limit on volume delivered. Drug delivery cannot be performed intravenously (IV) or by implantation of a continuous delivery device like a pump.

Animals: Heterozygote mice for the achondroplasia mutation, aged P4-P5, weighing approximately 3.5 gr. were randomly separated into groups of 3 animals/group and ear marked. Animals were distributed 6-7 individuals/cage with one foster mother.

Materials and Procedure: Animals were injected daily with drug intraperitoneally (IP) in a volume not exceeding 50 μl. This volume can be increased proportionally to weight increase. Animals are weighed and the tail length is measured on day 0 and every 2 days thereafter. The treatment is continued for 2 weeks. At the end of the administration period animals are sacrificed and skeletal elements are measured and analyzed by histology. CNP is administered at a concentration of $10^{-5}$ M and $10^{-6}$ M (in 1×PBS) during 2 weeks.

2. Administration of Drugs to Achondroplasia Model Mice using the Alzet Pump

Drug release by osmotic pumps provides a continuous supply and a constant amount of circulating drug. Furthermore, it enables directed release of the drug closer to the target site. Nevertheless, this procedure can only be performed in older mice.

Animals: Heterozygote mice for the achondroplasia mutation, aged P12-P14, weighing approximately 10 gr. were randomly separated into groups of 3 animals/group and ear marked. Animals were distributed 6-7 individuals/cage with one foster mother.

Materials and Procedure: The Alzet pumps used have a total volume of 100 µl and a release constant of 0.25 µl/hour over a course of 14 days. Pumps were filled with appropriate drug, calibrated for 4-6 hours, implanted subcutaneously (SC) on the back of anesthetized mice and the contents were directed with a catheter to the femoral artery of one hind limb. Mice were monitored for recovery and returned to mothers. Mice were weighed and measured every 2 days. At the end of the administration period animals were sacrificed and skeletal elements measured and analyzed by histology. This experiment was performed with a concentration of $10^{-4}$ M of CNP (in 1×PBS) in pump to obtain a concentration of $10^{-7}$ M in the blood stream.

Example 4

Implantation of Alginate Encapsulated Cells that Secrete CNP

Implantation of cells expressing high levels of NPs is a further method for providing a continuous source of NPs. NIH-3T3 fibroblasts were infected with retrovirus expressing mouse CNP and selected for resistance to neomycin. CNP secretion was tested by assaying the supernatant of the cells using RIA (RadioImmune Assay) specific for CNP (Phoenix Pharmaceuticals) and following manufacturer's instructions. The cells are encapsulated in APA (alginate-polylysine-alginate) complex according to the protocol described by Chang (Chang (1997) Ann N Y Acad Sci 831:461-73) and summarized below.

Materials and Methods:

1. Cell Preparation: Cells are removed from plate with trypsin, resuspended in media, transferred to 50 cc tube, spun down 5-10 minutes 100 rpm, media removed.

2. PBS Wash: Cells are resuspended in PBS, spun 5-10 minutes at 1000 rpm, PBS removed and cells resuspended in 0.5 ml PBS.

3. Alginate: Mix thoroughly with alginate, drawing completely in and then out>10 times, until a homogenous mix with no bubbles is seen.

4. Encapsulate cells: Extrude alginate-cell mix into 40 ml CaCl2 1.1% solution (on ice). Start with 1/10× until spray is invisible, then switch to 1/100×. Watch for accumulation of alginate on end of needle: either suction off or briefly increase extrusion rate to 1/10×. Determine the exact airflow for desired capsule size by checking capsule size/shape with check dishes. Routinely check capsules size/shape throughout process. Approximate settings: Extrusion: 99.9 at 1/100× speed, (brief 1/10× to force out blockages) Airflow of 3-4 yields large capsules (>600 um), 4-6 regular size capsules (generally 200-600 um), 6-8 small capsules (<200 um) 7-8 very small (50-100 um) and needle: 1-2 mm from end of airflow connector. Transfer capsules and CaCl2 solution to 50 cc conical tube.

5. Capsule washes: Allow capsules to settle. Remove supernatant with suction. Add wash solution, mix gently, and allow 2 minutes for capsules to settle.

6. Capsule implantation: The capsules are implanted intraperitoneally (IP) into P5 mice (Ach369 and wt). The mice are weighed and tail length measured every 2 days for 3 weeks.

Example 5

Co-Administration of CNP with an NEP Inhibitor

The NPs have been shown to have a short half-life in circulation, probably due to the activity of the neutral endopeptidase (NEP). We sought to block the activity of NEP with a specific inhibitor in order to increase the concentration of CNP in the blood.

The experiment is performed so that CNP is administered at $10^{-4}$ M via a pump to obtain a concentration of $10^{-7}$ M in blood stream together with thiorphan (NEP inhibitor) at a concentration of 10 mg/ml in pump (10 µg/ml blood stream) for 2 weeks. Administration is done by using an Alzet pump as described above. The same animals are injected IP with extra CNP daily ($10^{-7}$ M) together with 0.1% BSA. A similar experiment is performed with biotinylated BNP ($10^{-4}$ M, yielding $10^{-7}$ M in blood stream) injected daily, given in conjunction with thiorphan.

In a similar manner, any combination of NPs with compounds that contribute to NP stability in the circulation can be administered to a patient for efficient bone elongation and/or treatment of skeletal dysplasias. Such combinations may include a mixture of CNP and BNP, NPs in combination with peptidase inhibitors or in combination with NPR-C inhibitors. NP activity may be enhanced in combination with tyrosine kinase inhibitors.

Example 6

CNP Analogs

CNP is active as a 22 amino acid (22-mer) peptide (CNP 1-22), shown in FIG. 3 as SEQ ID NO:1. A shortened version of CNP, the 17 amino acid (17-mer) CNP 5-22 peptide, SEQ ID NO:2, was shown to be active in a cGMP assay. The 17-mer peptide comprises the amino acids of the cyclic domain of CNP and lacks five amino acids of the ectocyclic domain. NEP cleaves CNP at several sites, the primary one being the Cys6-Phe7 bond, as depicted by the thickened arrow in FIG. 3A. Peptide analogs were synthesized to obtain a less degradable, i.e. NEP resistant or NRP-C resistant, peptide by incorporating one or more amino acid substitutions. A set of peptides including those with amino acid deletions, insertions and substitutions is shown in Table 2. The 11mer to 15mer peptides were shown to have reduced cGMP activity.

In some peptides, a histidine residue was incorporated between Cys6 and Phe7 (His-CNP) to disrupt the cleavage recognition site. Other peptides were synthetically modified by methylation either on Phe7 only, or both on Phe7 and Leu11, sites of NEP activity. Peptides maybe modified by incorporation of a reporter molecule that allows detection, such as a biotin or fluorescein, at either the N-terminus or C-terminus of the peptide.

TABLE 2

Amino Acid Sequence of CNP Variants

| SEQ ID NO: | Amino Acid Sequence | % relative binding |
|---|---|---|
| 17-mers | | |
| SEQ ID NO:2 | C F G L K L D R I G S M S G L G C | 127.4 |
| SEQ ID NO:6 | C A G L K L D R I G S M S G L G C | 43.8 |
| SEQ ID NO:7 | C F G L K L A R I G S M S G L G C | 49.1 |
| SEQ ID NO:8 | C F G L K L D A I G S M S G L G C | 18.4 |
| SEQ ID NO:9 | C F G L K L D R A G S M S G L G C | 11.5 |
| SEQ ID NO:10 | C F G L K L D R I G S A S G L G C | 138.1 |
| 15-mers | | |
| SEQ ID NO:11 | C H F G L K L D R I G S M S – – C | 25.9 |
| SEQ ID NO:12 | C H F G L K L D R I G S M A – – C | 21.7 |
| SEQ ID NO:13 | C H F G L K L D R I G A Q S – – C | 26.5 |
| 14-mers | | |
| SEQ ID NO:14 | C F G L K L D R I G S M S – – – C | 29.9 |
| SEQ ID NO:15 | C F G L K L D R I G A Q S – – – C | 20.6 |
| 13-mers | | |
| SEQ ID NO:16 | C F G L K L D R I G S M – – – – C | 17.3 |
| SEQ ID NO:17 | C F G L K L D R I G A M – – – – C | 3.4 |
| SEQ ID NO:18 | C F G L K L D R I G S Q – – – – C | 11.8 |
| SEQ ID NO:19 | C F G L K L D R I G A Q – – – – C | 3.8 |
| SEQ ID NO:20 | C H F G L K L D R I G S – – – – C | 11.9 |
| 12-mers | | |
| SEQ ID NO:21 | C F G L K L D R I G S – – – – – C | 22.7 |
| 11-mers | | |
| SEQ ID NO:22 | C F G L K L D R I G – – – – – – C | 4.2 |
| SEQ ID NO:23 | C H F G L K L D R I – – – – – – C | 3.8 |

A substitution or incorporation of an amino acid is marked in bold and underlined. Amino acid deletions are marked as a dash.

All peptide variants were analyzed for activity using the Biotrak enzyme immunoassay (EIA, Amersham) that measures the amount of secondary messenger, cyclic GMP (cGMP), elicited after activation of the natriuretic peptide receptor by the peptide on C3H10T1/2 cells. Additional 17-mer variants were synthesized and tested with the results of the assay summarized in Table 3. Amino acid substitutions are marked in bold and underlined. The assay was performed for CNP and variants at a concentration of $10^{-6}$ M. The values are given as the percent of relative binding compared to CNP, where CNP 1-22 and CNP 5-22 yield 100% binding.

TABLE 3

CNP variants and in vitro cGMP values

| SEQ ID NO: | Amino acid sequence of CNP variants | % relative binding |
|---|---|---|
| SEQ ID NO:2 | C F G L K L D R I G S M S G L G C | 100.000 |
| SEQ ID NO:24 | C A G L K L A R I G S M S G L G C | -5.848 |
| SEQ ID NO:25 | C A G L K L D R I G S A S G L G C | 3.933 |

TABLE 3-continued

CNP variants and in vitro cGMP values

| SEQ ID NO: | Amino acid sequence of CNP variants | % relative binding |
|---|---|---|
| SEQ ID NO:26 | C F G L K L A R I G S A S G L G C | 5.755 |
| SEQ ID NO:27 | C A G L K L A R I G S A S G L G C | -10.355 |
| SEQ ID NO:28 | C I G L K L D R I G S M S G L G C | 13.899 |
| SEQ ID NO:29 | C L G L K L D R I G S M S G L G C | 6.255 |
| SEQ ID NO:30 | C M G L K L D R I G S M S G L G C | -1.341 |
| SEQ ID NO:31 | C W G L K L D R I G S M S G L G C | -10.834 |
| SEQ ID NO:32 | C V G L K L D R I G S M S G L G C | 5.740 |
| SEQ ID NO:33 | C H G L K L D R I G S M S G L G C | 5.699 |
| SEQ ID NO:34 | C T G L K L D R I G S M S G L G C | -6.903 |
| SEQ ID NO:35 | C F G L K L E R I G S M S G L G C | 9.450 |
| SEQ ID NO:36 | C F G L K L Q R I G S M S G L G C | -17.095 |
| SEQ ID NO:37 | C F G L K L N R I G S M S G L G C | 17.235 |
| SEQ ID NO:38 | C F G L K L I R I G S M S G L G C | 7.228 |
| SEQ ID NO:39 | C F G L K L M R I G S M S G L G C | 7.784 |
| SEQ ID NO:40 | C F G A K L D R I G S M S G L G C | 20.154 |
| SEQ ID NO:41 | C F G I K L D R I G S M S G L G C | 47.395 |
| SEQ ID NO:42 | C F G V K L D R I G S M S G L G C | 64.212 |
| SEQ ID NO:43 | C F G L L L D R I G S M S G L G C | 29.744 |
| SEQ ID NO:44 | C F G L M L D R I G S M S G L G C | 5.421 |
| SEQ ID NO:45 | C F G L K A D R I G S M S G L G C | 11.259 |
| SEQ ID NO:46 | C F G L K I D R I G S M S G L G C | 88.117 |
| SEQ ID NO:47 | C F G L K V D R I G S M S G L G C | 66.714 |
| SEQ ID NO:48 | C F G L K L D H I G S M S G L G C | 13.482 |
| SEQ ID NO:49 | C F G L K L D K I G S M S G L G C | 21.543 |
| SEQ ID NO:50 | C F G L K L D Q I G S M S G L G C | 11.953 |
| SEQ ID NO:51 | C F G L K L D R L G S M S G L G C | 14.177 |
| SEQ ID NO:52 | C F G L K L D R V G S M S G L G C | 27.103 |
| SEQ ID NO:53 | C F G L K L D R T G S M S G L G C | -1.945 |
| SEQ ID NO:54 | C F G L K L D R I G A M S G L G C | 54.469 |
| SEQ ID NO:55 | C F G L K L D R I G G M S G L G C | 27.811 |
| SEQ ID NO:56 | C F G L K L D R I G T M S G L G C | 74.080 |
| SEQ ID NO:57 | C F G L K L D R I G N M S G L G C | 27.430 |
| SEQ ID NO:58 | C F G L K L D R I G S M S A L G C | 53.649 |
| SEQ ID NO:59 | C F G L K L D R I G S M S L L G C | 15.289 |
| SEQ ID NO:60 | C F G L K L D R I G S M S K L G C | 49.202 |
| SEQ ID NO:61 | C F G L K L D R I G S M S G Q G C | -3.474 |
| SEQ ID NO:62 | C F G L K L D R I G S M S G M G C | 51.286 |

TABLE 3-continued

CNP variants and in vitro cGMP values

| SEQ ID NO: | Amino acid sequence of CNP variants | % relative binding |
|---|---|---|
| SEQ ID NO:63 | C F G L K L D R I G S M S G A G C | -1.111 |
| SEQ ID NO:64 | C F G L K L D R I G S M S G G G C | -10.145 |
| SEQ ID NO:65 | C F G L K L D R I G S W S G L G C | 66.450 |
| SEQ ID NO:66 | C F G L K L D R I G S H S G L G C | 66.222 |
| SEQ ID NO:67 | C F G L K L D R I G S K S G L G C | 66.910 |
| SEQ ID NO:68 | C F G L K L D R I G S S S G L G C | 62.531 |
| SEQ ID NO:69 | C F G L K L D R I G S G S G L G C | 62.117 |
| SEQ ID NO:70 | C H G L K L D R I G S A S G L G C | 3.058 |
| SEQ ID NO:71 | C T G L K L D R I G S A S G L G C | -9.108 |

The peptide of SEQ ID NO: 2 was shown to be as active as the native CNP1-22, SEQ ID NO: 1. The modification lies in the removal of the N-terminal amino acids, the ectocyclic part of the peptide. The peptide of SEQ ID NO: 10 contains a substitution of Met17 with Ala. This variant retains high activity perhaps due to the alteration of an NEP cleavage site. Furthermore, the peptide of SEQ ID NO: 10 was tested in bone culture and shown to induced elongation of Ach369 femora even at a concentration similar to that of CNP.

The peptide variant of SEQ ID NO: 6 has an amino acid substitution whereby Phe7 is modified to Ala. All tested substitutions of the Phe7, SEQ ID NOs: 24-25, 27-34 and 69-71, resulted in reduced activity.

Another modification includes a gain of activity obtained by the substitution of Met17. Met 17 is a site of NEP cleavage and its substitution by another amino acid including Ala identified as SEQ ID NO:10 increases activity and may increase stability. Other substitutions of Met retaining activity are Trp His, Lys, Ser and Gly identified herein as SEQ IS Nos:65-69. Other examples of variants wherein modifications were directed to the cleavage sites and activity is retained are disclosed as SEQ ID NOs: 45-47 wherein Leu10 is substituted, SEQ ID NOs:54-57 wherein Ser16 is substituted and SEQ ID Nos:58-60 wherein Gly19 is substituted.

Peptide variants exhibiting a high level of activity as determined in the cGMP assay may be useful for treating skeletal disorders. These variants may be useful alone or in combination with other compounds including but not limited to NPs, NEP inhibitors, NPR-C inhibitors or TK inhibitors. The variants with reduced activity may be useful alone or in conjugation with other NPs and may impart stability or synergy.

One skilled in the art will recognize that the variants may be synthesized as peptide mimetics. A peptide mimetic or peptidomimetic, is a molecule that mimics the biological activity of a peptide but is not completely peptidic in nature. Whether completely or partially non-peptide, peptidomimetics provide a spatial arrangement of chemical moieties that closely resembles the three-dimensional arrangement of groups in the peptide on which the peptidomimetic is based. As a result of this similar active-site geometry, the peptidomimetic has effects on biological systems which are similar to the biological activity of the peptide.

Example 7 in vivo Assays

Methods for detecting administered compounds in the blood or tissue of treated mammals are known in the art. The pharmacokinetic properties of the administered compounds are determined using such methods. In animal models, radiolabelled oligonucleotides or peptides can be administered to and their distribution within body fluids and tissues assessed by extraction of the oligonucleotides or peptides followed by autoradiography (Agrawal et al (1991) PNAS 88:7595-99). Other methods include labeling of a peptide with a reporter moiety, including fluorescent or enzyme labels, administration to an animal, extraction of the peptide from body fluids and organs followed by HPLC analysis. Alternatively, immunohistochemical methods are used for detection of the administered peptide in tissue. The present invention contemplates reporter labeled NPs and CNP variants.

Example 8

GH-CNP Fusion Construct

One approach to creating high local concentrations of a therapeutic molecule is to target it to the growth plate (GP) via a GP-specific carrier including but not limited to growth hormone (GH), IGF-1, TH and receptor ligands. GH is an endocrine hormone that is secreted by the pituitary and affects bone elongation. Targeted delivery of a compound into cells comprising a chimeric protein has been disclosed for example in US Patent Application No. 20010025026.

Figure 4:
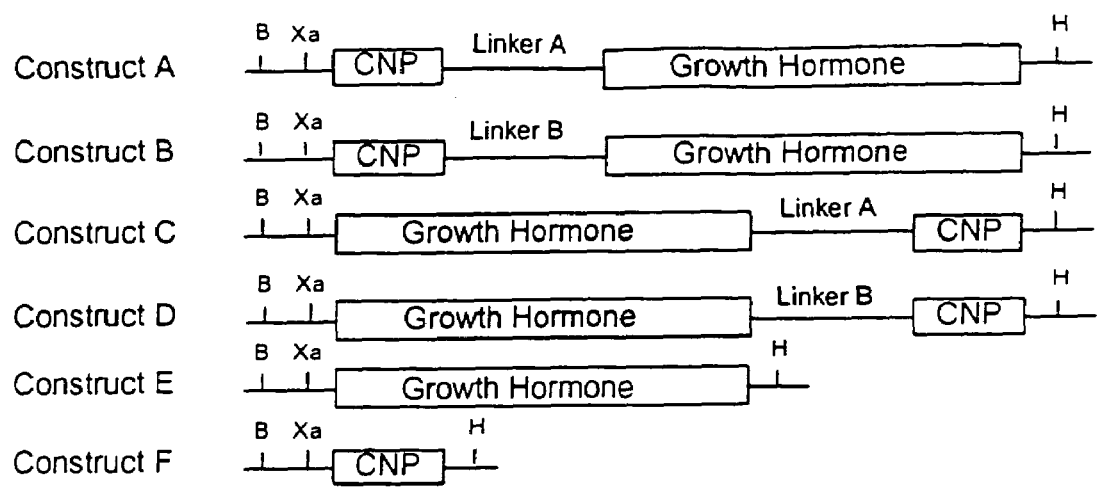
FIG. 4 shows a scheme of the growth hormone-CNP constructs for producing GH-CNP fusion protein.

We have synthesized a GH-CNP fusion construct useful as a carrier for CNP on its way into the growth plate. This fusion protein maintains the binding capacity of GH and the activity of CNP. In one aspect a linker has been added between the two peptides which enables independent folding of each part. In another aspect, a linker comprising a cleavage site has been introduced to allow physical separation of the two hormones. FIG. 4 shows a scheme of the constructs.

To determine whether GH can enter the growth plate from the circulation, GH was labeled with $^{125}$Iodine and administered to mice IP, one hour after a pulse of unlabelled GH. Blood samples were collected at several time points and analyzed on a protein gel. The samples show strong labeling which increases in the first 2-3 hours, can still be observed at 6 hours and almost disappears at 24 hrs.

PCR and Cloning: Mouse Growth Hormone (mGH) and mouse CNP (mCNP) were isolated from a brain cDNA library by method of RT-PCR, using the following oligonucleotide primers (oligos):

Mouse Growth Hormone:

```
                                        (SEQ ID NO: 72)
For:   5' TGG CAA TGG CTA CAG ACT CTC GG (SEQ ID NO: 73)
Rev:   5' GAA GGC ACA GCT GCT TTC CAC AA
```

Mouse CNP:

```
                                        (SEQ ID NO: 74)
For:   5' ACC CAA GCT TAT GCA CCT CTC CCA GC (SEQ ID NO: 75)
Rev:   5' CCA TCG ATC TAA CAT CCC AGA CCG
```

The generated PCR products were sub-cloned into plasmids and sequenced to verify their identity and fidelity. These plasmids were then used as templates for the generation of the fusion constructs which were generated by a two-step nested PCR approach. The construction is described in detail here, using four different oligonucleotides and three PCR reactions. All other constructs were generated by similar methodology. Construct A harbors sequences encoding:
BamHI-Factor Xa Cleavage Site-mCNP-Linker A-mGH-Stop Codon-Hind III.

The first PCR reaction (21 cycles) was performed on mCNP using the forward oligo which harbors sequences to encode a BamHI cloning site, Factor Xa consensus cleavage site as well as the 5' of mouse CNP and the reverse oligo which harbors the 3' component of CNP, as well as sequences to encode linker A. The second PCR reaction (21 cycles) was performed on mGH using forward oligo which harbors sequences to encode a linker A as well as the 5' of mGH and a reverse oligonucleotide which harbors the 3' component of mGH, including a stop codon and a HindIII site for subsequent sub-cloning. The third PCR reaction (21 cycles) was performed by combining the products of the two above PCR reactions, the forward oligo from the first PCR reaction, the reverse oligo from the second PCR reaction. The overlapping linker sequences for the two different template DNAs, allowed the generation of the full-length fusions. The constructs were cloned into an expression vector and used to transfect host cells. The fusion proteins were synthesized and isolated according to methods known in the art.

A construct wherein the CNP lies 5' to the mGH was constructed, as well. A scheme of all the constructs that have been made is shown in FIG. 4. The legend for FIG. 4 is as follows: Linker A is a simple flexible linker encoding six amino acids: Gly Gly Ser Gly Gly Ser while Linker B harbors an MMP9-specific cleavage sequence (Kridel et al. (2001) J Biol Chem 276: 20572-8). B and H are BamHI and HindIII restriction enzyme sites, respectively and Xa is a factor Xa cleavage site.

The activity of the GH and CNP in the fusion protein is assessed by measurement of cGMP accumulation for CNP and activity of GH.

Example 9

Establishment of Assay to Assess Resistance to NEP Degradation

Endothelial cells express neutral endopeptidase (NEP) in vivo and thus degrade part of the circulating natriuretic peptides. An in vitro assay has been established to determine the stability of the modified peptides in the presence of endopeptidases. Endothelial cell lines have been used but any primary cell or cell line expressing NEP may be useful in the assay. Endothelial cell lines derived from either bovine or human tissue are grown. Cells are overlayed with $10^{-6}$ M CNP or variant, incubated overnight and the medium is assayed for cGMP activity, as described above. The results obtained from the variants are compared to the activity of CNP.

Example 10

Establishment of Assay to Assess Resistance to NPR-C Degradation

An assay to determine the resistance of the CNP variants to clearance via the NPR-C receptor is being established using astrocytes derived from a NPR-C knockout mouse (Matzukawa et al (1999) PNAS 96:7403-8).

It will be evident to the skilled artisan that administration of NPs according to the principles of the present invention can be performed by any suitable route of administration, utilizing any suitable pharmaceutically acceptable carrier or diluent. Under certain circumstances specific formulations that enable or enhance targeting of the active principle to the bone or growth plate may be utilized such as but not limited to use of the NPs in combination with vehicles such as liposomes, microemulsions, microcapsules, microspheres, and the like. It is also intended antibodies, peptides, hydroxyapatite, glucosarnine, collagen especially collagen type X, polyGlu or polyAsp and other molecules having affinity for the growth plate.

It will be appreciated that many improvements may be achieved by stabilization of the NP or otherwise achieving a prolonged half life or improved pharmacokinetic profile. For example, functional variants of NPs having enhanced stability in vivo, such as peptides having altered sequences or configurations, may be administered for treatment of skeletal dysplasias and/or bone elongation.

Further, cells can be engineered to produce and secrete functional variants of NPs having enhanced stability in vivo and these cells may be encapsulated in APA (alginate-polylysine-alginate) complex and implanted intraperitoneally for treatment of skeletal dysplasias and/or bone elongation.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A pharmaceutical composition for bone elongation or treating skeletal dysplasias comprising at least one natriuretic peptide variant set forth in SEQ ID NO:5 wherein Xaa=Leu, Ile, Val; Xbb=Lys, Leu, Met; Xcc=Leu, Ile, Ala, Val; Xdd=Ser, Ala, Gly, Thr, Asn; Xee=Ala, Trp, His, Lys, Ser, Gly; Xff=Gly, Lys, Ala, Leu; and Xgg=Leu, Met, and a carrier or excipient, wherein SEQ ID NO:5 is other than amino acid sequence set forth in SEQ ID NO:2.

2. The pharmaceutical composition according to claim 1 further comprising an inhibitor of the natriuretic peptide clearance receptor.

3. The pharmaceutical composition according to claim 1 further comprising an inhibitor of the neutral endopeptidase 24.11.

4. The pharmaceutical composition according to claim 3 wherein the inhibitor of neutral endopeptidase 24.11 is thiorphan or candoxatril.

5. The pharmaceutical composition according to claim 1 further comprising an inhibitor of fibroblast growth factor receptor 3 tyrosine kinase.

6. The pharmaceutical composition according to claim 1 wherein the natriuretic peptide is fused to a carrier protein forming a natriuretic peptide-carrier protein fusion protein; wherein the carrier protein is selected from the group consisting of growth hormone (GH), insulin like growth factor-1 (1GF-1) and thyroid hormone (TH).

7. The pharmaceutical composition according to claim 6 wherein the carrier protein comprises growth hormone.

8. The pharmaceutical composition according to claim 6 wherein said at least one natriuretic peptide is conjugated to a carrier protein forming a natriuretic peptide-carrier protein conjugate.

9. A method for increasing the size of a bone growth plate in a bone comprising treating the bone in vitro with an effective amount of at least one natriuretic peptide in a pharmaceutical composition according to claim 1.

10. The method according to claim 9 further comprising inhibiting the natriuretic peptide clearance receptor.

11. The method according to claim 9 further comprising an inhibitor of the neutral endopeptidase 24.11.

12. The method according to claim 11 wherein the inhibitor of neutral endopeptidase 24.11 is thiorphan or candoxatril.

13. The method according to claim 12 wherein the step of administering an inhibitor of neutral endopeptidase is performed simultaneously with the step of administering an effective amount of at least one natriuretic peptide.

14. The method according to claim 9 further comprising an inhibitor of fibroblast growth factor receptor 3 tyrosine kinase.

15. The method according to claim 9 wherein said at least one natriuretic peptide is fused to a carrier protein forming a natriuretic peptide-carrier protein fusion protein protein wherein the carrier protein is selected from the group consisting of growth hormone (GH), insulin like growth factor-1(1GF-1) and thyroid hormone (TH).

16. The method according to claim 15 wherein the carrier protein fusion protein comprises growth hormone.

17. The method according to claim 9 wherein said at least one natriuretic peptide is conjugated to a carrier protein forming a natriuretic peptide-carrier protein conjugate.

18. The method according to claim 9 wherein the bone is a limb bone.

19. The method according to claim 18 wherein the limb bone is an achondroplasic bone.

20. A method for elongation of bone, comprising treating the bone in vitro with an effective amount of at least one natriuretic peptide in a pharmaceutical composition according to claim 1.

21. The method according to claim 20 further comprising inhibiting the natriuretic peptide clearance receptor.

22. The method according to claim 20 further comprising an inhibitor of the neutral endopeptidase 24.11.

23. The method according to claim 22 wherein the inhibitor of neutral endopeptidase 24.11 is thiorphan or candoxatril.

24. The method according to claim 22 wherein the step of administering an inhibitor of neutral endopeptidase is performed simultaneously with the step of administering an effective amount of at least one natriuretic peptide.

25. The method according to claim 20 further comprising an inhibitor of fibroblast growth factor receptor 3 tyrosine kinase.

26. The method according to claim 20 wherein said at least one natriuretic peptide is a natriuretic peptide fused to a carrier protein forming a natriuretic peptide-carrier protein fusion protein.

27. The method according to claim 20 wherein the carrier protein comprises growth hormone.

28. The method according to claim 20 wherein said at least one natriuretic peptide is conjugated to a carrier protein forming a natriuretic peptide-carrier protein conjugate wherein the carrier protein is selected from the group consisting of growth hormone (GH), insulin like growth factor-1(1GF-1) and thyroid hormone (TH).

29. The method according to claim 20 wherein the bone is a limb bone.

30. The method according to claim 20 wherein the limb bone is an achondroplasic bone.

* * * * *

UNITED STATES PATENT AND TRADEMARK OFFICE
CERTIFICATE OF CORRECTION

PATENT NO. : 7,276,481 B2  
APPLICATION NO. : 10/664605  
DATED : October 2, 2007  
INVENTOR(S) : Golembo et al.

Page 1 of 1

It is certified that error appears in the above-identified patent and that said Letters Patent is hereby corrected as shown below:

Title Page:  
Before Item (30), please insert the following:  
-- (60) Provisional application No. 60/276,939, filed Mar. 20, 2001. --

Column 51:  
Line 9 (claim 6, line 6), change "(1GF-1)" to -- (IGF-1) --.  
Line 17 (claim 9, line 2), before "in vitro", change "hone" to -- bone --.  
Line 36 (claim 15, line 3), after "protein fusion", delete the second occurrence of "protein".  
Line 39 (claim 15, line 6), change "(1GF-1)" to -- (IGF-1) --.

Column 52:  
Line 5 (claim 20, line 1), before "bone" insert -- a --.  
Line 30 (claim 27, line 1), after "claim", change "20" to -- 26 --.  
Line 37 (claim 28, line 6), change "(1GF-1)" to -- (IGF-1) --.

Signed and Sealed this

Eleventh Day of December, 2007

JON W. DUDAS  
*Director of the United States Patent and Trademark Office*